United States Patent [19]
Cantegril et al.

[11] Patent Number: 5,945,382
[45] Date of Patent: *Aug. 31, 1999

[54] FUNGICIDAL ARYLPYRAZOLES

[75] Inventors: Richard Cantegril, Lyons; Denis Croisat, Paris; Philippe Desbordes, Lyons; François Guigues, Rillieux-la-Pape; Jacques Mortier, La Bouëxier; Raymond Peignier, Caluire; Jean Pierre Vors, Lyons, all of France

[73] Assignee: Rhone-Poulenc Agrochimie, Lyons, France

[ * ] Notice: This patent is subject to a terminal disclaimer.

[21] Appl. No.: 08/325,283

[22] PCT Filed: Apr. 26, 1993

[86] PCT No.: PCT/FR93/00403

§ 371 Date: Dec. 22, 1994

§ 102(e) Date: Dec. 22, 1994

[87] PCT Pub. No.: WO93/22287

PCT Pub. Date: Nov. 11, 1993

[30] Foreign Application Priority Data

Apr. 27, 1992 [FR] France .................................. 92 05434

[51] Int. Cl.$^6$ ........................ A01N 43/56; A61K 31/415; C07D 231/12
[52] U.S. Cl. ........................ 504/280; 514/406; 548/377.1
[58] Field of Search ........................ 548/377.1; 514/406; 504/280

[56] References Cited

U.S. PATENT DOCUMENTS

| | | | |
|---|---|---|---|
| 2,721,143 | 10/1955 | Kraft et al. | 99/222 |
| 2,946,765 | 7/1960 | Roos et al. | 548/377.1 |
| 3,072,525 | 1/1963 | Neumann | 167/31 |
| 3,658,838 | 4/1972 | Kiehne et al. | 260/310 R |
| 4,008,249 | 2/1977 | Fischer et al. | 548/377.1 |
| 4,055,409 | 10/1977 | Johnson et al. | 548/377.1 |
| 4,072,498 | 2/1978 | Moon et al. | 71/92 |
| 4,477,462 | 10/1984 | Aoyagi | 424/273 P |
| 4,792,565 | 12/1988 | Shimotori et al. | 514/406 |
| 5,134,142 | 7/1992 | Matsuo et al. | 514/255 |
| 5,342,835 | 8/1994 | Pepin et al. | 514/227.5 |
| 5,523,280 | 6/1996 | Chene et al. | 504/280 |
| 5,663,119 | 9/1997 | Chene et al. | 504/280 |

FOREIGN PATENT DOCUMENTS

| | | |
|---|---|---|
| 0360701 | 3/1990 | European Pat. Off. . |
| 1152109 | 8/1963 | Germany . |
| 42-11944 | 7/1967 | Japan . |
| 42-11945 | 7/1967 | Japan . |
| 59-53468 | 3/1984 | Japan . |
| 2300173 | 12/1990 | Japan . |
| 2224208 | 5/1990 | United Kingdom . |

OTHER PUBLICATIONS

English translation of JP 2–300173, 1990.
English translation of JP 59–53468, 1984.
English translation of JP 3–93774, 1991.
Miura et al., (CA 114:164226), 1991.
Miura et al., (CA 115:92260), 1991.
Chemical Abstracts, vol. 108, No. 23, 1986, abstract No. 204577b.
CAS Registry Handbook, No. section, RN=114913–44–9, 114486–01–0, 99067–15–9, 113140–19–5, 73227–97–1, 27069–17–6, 18099–21–3, 17978–27–7, 1988.
Hattori et al., CA 68:68981 (1968), Registry No. 17978–25–5, 17978–26–6, 17978–27–7 and 18099–21–3.
Hattori et al., CA 68:68982 (1968), Registry No. 17978–28–8.
Janssen et al., CA 78:159514 (1973), Registry No. 38858–97–8 and38859–02–8.
Chang et al., CA 92:146667 (1980), Registry No. 73227–91–1.
Berenyi et al., CA 94:156963 (1981), Registry No. 77197–10–5.
Markwell et al., CA 108:112444 (1988), Registry No. 113140–19–5.
Maslova et al., CA 119:8733 (1993), Registry No. 147993–04–2.
Maslova et al., Khim. Farm. Zh. (1992), 26(11–12), pp. 77–81, Registry No. 147993–04–2.

Primary Examiner—Laura L. Stockton
Attorney, Agent, or Firm—Burns, Doane, Swecker & Mathis, L.L.P.

[57] ABSTRACT

The present invention relates to new derivatives of the family of 3-arylpyrazoles of formula (I), their methods of preparation, the compositions containing them and their utilization for the protection of plants against fungal diseases.

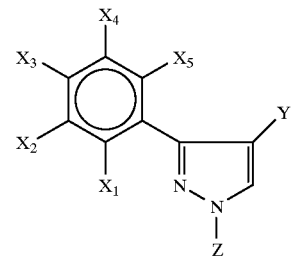

15 Claims, No Drawings

FUNGICIDAL ARYLPYRAZOLES

This application is a 371 of PCT/FR93/00403 filed Apr. 26, 1993.

The present invention relates to new derivatives of the 3-arylpyrazole family, to the processes for their preparation, to the compositions containing them and to their use for protecting plants against fungal diseases.

More specifically, the subject of the invention is 3-arylpyrazole derivatives, characterised in that they are of formula I:

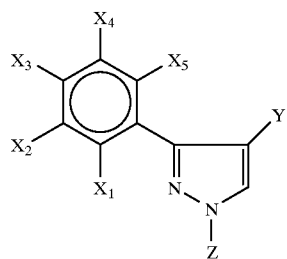

in which:

$X_1$, $X_2$, $X_3$, $X_4$ and $X_5$, which are identical or different, are:

a hydrogen or halogen atom, or a hydroxyl, cyano, thiocyanato, nitro, nitroso or amino group, the amino group optionally being substituted by one or two alkyls or phenyls, an alkyl, hydroxyalkyl, alkoxyalkyl, alkylthioalkyl, alkylsulphinylalkyl, alkylsulphonylalkyl, benzyl, alkenyl, alkynyl, cyanoalkyl, alkoxy, alkenoxy, alkylthio, formyl, acetyl, alkylcarbonyl, alkoxy(thio)carbonyl, mono- or dialkylamino(thio)carbonyl, iminocarbonyl, mono- or diarylamino(thio)carbonyl, carboxyl, carboxylate, carbamoyl or benzoyl radical, a phenyl, phenyloxy or phenylthio radical, an alkyl- or alkoxy- or monoalkylamino- or dialkylamino- or phenylsulphenyl or -sulphinyl or -sulphonyl, a phosphoryl group, substituted by two groups chosen from the group comprising alkyl, alkoxy, alkylthio and dialkylamino, benzyloxy, phenyloxy or phenyl, a trialkylsilyl or alkylphenylsilyl group, Two of the adjacent $X_1$, $X_2$, $X_3$, $X_4$ and $X_5$ groups can also be connected to each other via a carbon bridge comprising 2 to 4 members, one at least of which can be replaced by an oxygen, sulphur or nitrogen atom, it being possible for the carbons of this bridge to be unsubstituted or substituted by at least one halogen atom and/or at least one hydroxyl, amino, alkyl, alkoxy, alkylthio, mono- or dialylamino, or alkylsulphinyl or -sulphonyl group, the alkyl part being as defined above, with the proviso that $X_1$ to $X_5$ and $X_3$ to $X_5$ cannot be each simultaneously a hydrogen atom; $X_1$ and Y is a hydrogen or halogen atom or a nitro, nitrile, thiocyanato or alkyl, alkoxy or alkylthio, or alkylsulphinyl or alkylsulphonyl group, the alkyl part of these radicals being optionally mono- or polyhalogenated, or an amino optionally substituted by one or two alkyls or phenyls;

Y and $X_1$ or $X_5$ can also be connected to each other via a carbon bridge comprising 5 to 7 members, one at least of which can be replaced by an oxygen, sulphur or nitrogen atom, it being possible for the carbons of this bridge to be unsubstituted or substituted by at least one halogen atom and/or at least one hydroxyl, alkoxy, alkylthio, mono- or dialylamino, or alkylsulphinyl or -sulphonyl group, the alkyl part being as defined above, Z is:

a hydrogen or halogen atom or a cyano, nitro or hydroxyl group or alkyl, haloalkyl, cycloalkyl or cycloalkylalkyl, it being possible for the cycloalkyl part to be substituted by the group $GR_4$, defined below, or alkoxy, optionally substituted by a hydroxyl, an alkoxy or an alkylthio; or an alkylthio, a phenyloxy or phenylthio, an amino optionally substituted by one or two alkyls or optionally substituted alkenyl or alkynyl, each containing from 3 to 7 carbon atoms optionally substituted phenyl or Het, a group of formula $C(Z_1)Z_2$ in which:

$Z_1$ is an oxygen or sulphur atom or an alkylamino or imino or arylamino group and $Z_2$ is:
a hydrogen or halogen atom or a hydroxyl, thiol, cyano or amino group,
alkyl, alkoxy or alkylthio,
alkenyl or alkynyl, each containing from 3 to 7 carbon atoms
phenyl, phenylalkyl, phenoxy, phenalkyloxy,
Het or Het-alkyl,
phenylalkenyl or phenylalkynyl; Het-alkenyl or Het-alkynyl
mono- or dialkylamino, or a mono- or diphenyl-amino or
sulphonylamino radical, a phosphoryl group substituted by two radicals chosen from the group comprising alkyl, alkoxy, alkylthio, dialkylamino, cycloalkyl or cycloalkylalkyl, alkenyl or alkynyl, phenyl, phenylalkyl, Het or Het-alkyl, phenyl or Het, optionally substituted;

or a group $S(Z_1)(Z_3)Z_2$, in which $Z_1$ and $Z_2$ have the same meanings as above and $Z_3$ has the same meanings. without necessarily being equal to $Z_1$, with the proviso that Z is not a hydrogen atom when $X_3$, $X_4$ and $X_5$ are each a hydrogen atom;

and the tautomeric forms of formula Ia, when Z is a hydrogen atom or a group of formula $C(Z_1)Z_2$, or $S(Z_1)(Z_3)Z_2$

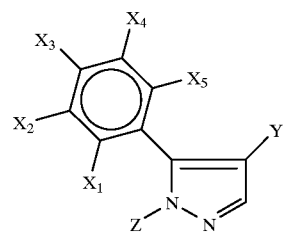

their hydracid or perchloric or nitric or sulphuric acid or alkyl- or (optionally substituted)phenylsulphonic acid salts and their metal or metalloid complexes, it being understood that in all the meanings above,
the hydrocarbon part of these groups can comprise from 1 to 7 carbon atoms and can be optionally halogenated (from 1 to 8 halogen atoms), the cycloalkyl part of these groups can comprise from 3 to 7 carbon atoms and can be optionally substituted by at least one substituent chosen from the group $GR_4$, the phenyl part denotes the phenyl ring optionally substituted by 1 to 5 substituents chosen from the group comprising a halogen atom or an alkyl or alkoxy containing 1 to 3 carbon atoms, Het is a mono- or bicyclic heterocyclic radical containing from 5 to 10 atoms, 1 to 4 of which are heteroatoms (oxygen, sulphur, nitrogen or phosphorus).

Preferably, in the formula, Y is a chlorine or bromine atom.

Other preferred derivatives are such that, in the formula I, Z is a hydrogen or a group $C(Z_1)Z_2$, in which $Z_1$ is an oxygen or sulphur atom.

Other preferred derivatives are such that, in the formula I, $X_1$, $X_2$ and $X_4$ are a hydrogen or halogen atom or a nitro group or an optionally halogenated alkyl group containing 1 to 4 carbon atoms.

Other preferred derivatives are such that, in the formula I, $X_3$ is a hydrogen or fluorine atom.

Other preferred derivatives are such that, in the formula I, $X_5$ is a hydrogen atom.

Other preferred derivatives are such that, in the formula I, two adjacent substituents chosen from $X_1$, $X_2$, $X_3$, $X_4$ and $X_5$ form a bridge comprising 3 or 4 members, in particular an optionally halogenated and preferably fluorinated methylenedioxy bridge.

The compounds of formula I, in which Z is $C(Z_1)Z_2$ or $S(Z_1)(Z_3)Z_2$, in which $Z_1$ or $Z_3$ is an oxygen or sulphur atom, can be prepared, in a way known per se, by reaction of a derivative of formula II:

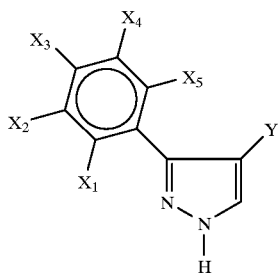

II with an acylating agent as described in the compilations "Comprehensive Heterocyclic Chemistry", A. R. Katritzky and C. W. Rees, 1984, Vol. 5, pages 222 to 242, Pergamon Press and in "The Chemistry of Heterocyclic Compounds", L. C. Behr, R. Fusco and C. H. Jardoe, 1967, pages 137 to 140, J. Wiley & Sons, 1966, Vol. 6, pages 391 to 396, Academic Press and "The Chemistry of Heterocyclic Compounds", L. C. Behr, R. Fusco and C. H. Jardoe, 1967, pages 84 to 91 and Table 41, J. Wiley & Sons.

Acylating agent is understood to mean a compound of formula $Z_4C(Z_1)Z_2$ or $Z_5S(Z_1)(Z_3)Z_2$, in which $Z_1$, $Z_2$ and $Z_3$ are defined as above and $Z_4$ and $Z_5$ are chosen from the group comprising a halogen atom or a hydroxyl, alkoxy, alkylthio, amino, monoalkylamino or dialkylamino group, the alkyl part of these groups containing from 1 to 4 carbon atoms.

The derivatives of formula II according to the invention can be prepared using various processes known per se especially in the compilations "Comprehensive Heterocyclic Chemistry", A. R. Katritzky and C. W. Rees, 1984, Vol. 5, pages 239 to 241 and 263, Pergamon Press; "Advances in Heterocyclic Chemistry", A. N. Kost and I. I. Grandberg, 1966, Vol. 6, pages 391 to 396, Academic Press and "The Chemistry of Heterocyclic Compounds", L. C. Behr, R. Fusco and C. H. Jardoe, 1967, J. Wiley & Sons.

A first process for the manufacture of the compounds of formula II, in which Z is a hydrogen atom and Y is a halogen atom, consists in reacting a 3-arylpyrazole of formula III:

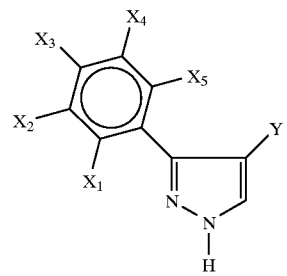

in which $X_1$, $X_2$, $X_3$, $X_4$ and $X_5$ and Z have the same meaning as in the formula I and Y is a hydrogen atom, with a halogenating agent.

As halogenating agents, there may be mentioned, as chlorinating agent, chlorine, preferably in aqueous medium such as water, or organic medium such as acetic acid or carbon tetrachloride, or else hypochlorous acid, hydrochloric acid in the presence of hydrogen peroxide in acetic acid, or else sulphuryl chloride or a N-chloroimide such as N-chlorosuccinimide in a chlorinated solvent such as dichloromethane, or else phosphorus pentachloride.

The chlorination can be carried out with chlorine in organic solvent medium, preferably a lower carboxylic acid, at a temperature of 16 to 30° C., and preferably at room temperature, the reactants being in a substantially stoichiometric molar ratio. The chlorination can also be carried out with N-chlorosuccinimide in organic solvent medium, preferably a chlorinated solvent such as dichloromethane or 1,2-dichloroethane, at a temperature of 0° C. to 80° C., and preferably of 20° C. to 50° C., the reactants being in a substantially stoichiometric molar ratio.

As brominating agent, there may be mentioned bromine, preferably in an aqueous solvent such as water, in acidic medium, for example nitric or acetic, in the presence or absence of a base such as sodium acetate, or in an organic solvent such as, for example, chloroform, or else pyridinium perbromide.

The bromination can be carried out, for example, with bromine in an organic solvent medium such as a lower carboxylic acid, at a temperature of 16° C. to, preferably at room temperature.

As iodinating agent, there may be used iodine in the presence of hypoiodous acid or in the presence of a base such as an alkali metal hydroxide or a basic salt such as sodium acetate, or in the presence of a nickel(II) salt; it is also possible to use iodine on the silver(I) salt of the pyrazole of formula III.

Fluorination can be carried out from derivatives of formula II in which Y is an amino group by preparation of the diazonium tetrafluoroborate derivative derived from the amino group and then irradiation of this compound.

A second process known per se for the preparation of the derivatives of formula II according to the invention, in which Y is a bromine atom, consists in reacting a compound of formula II, in which Y is a formyl group, with bromine in acetic acid to give the 4-bromo-3-phenylpyrazole.

The enaminone compounds of formula III can be prepared, in a way known per se, by reaction of a derivative of formula IV:

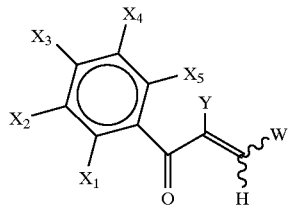

in which W is a hydroxyl radical or a chlorine atom or a monoalkylamino or dialkylamino or phenylamino group and $X_1$ to $X_5$ have the same meanings as in the formula I, with hydrazine hydrate, at a temperature of 10° C. to 150° C., preferably of 20° C. to 120° C., advantageously in an organic solvent medium, preferably a lower carboxylic acid or in an alcohol, in the presence of an organic or inorganic acidic catalyst, the molar ratio of the two reactants being substantially stoichiometric.

The compounds of formula IV, in which W is a dialkylamino group, $X_1$ to $X_5$ being defined as above, can be obtained, in a way known per se, by reaction of acetophenones of formula V:

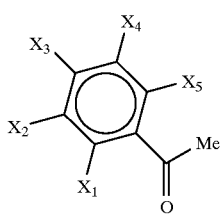

in which $X_1$ to $X_5$ are defined as above, with amide acetals, ester aminals or orthoaminals, preferably in the absence of an organic solvent with dialkyl (preferably dimethyl or diethyl) acetals of N,N-dimethylformamide, at a temperature of 20° C. to 130° C. and preferably of 70° C. to 130° C.

The acetophenones of formula V are for the most part commercially available. Those which are not can be prepared in a way known per se
- either a) (C.Atkinson et al., J. Chem. [lacuna] 1983: Vol. 26, 1353; W. F. Beech in J. Chem. Soc., 1954, 1297) by reaction of acetaldoxime or of one of its O-substituted derivatives, or of acetaldehyde hydrazone or of one of its N-substituted derivatives, in the presence of copper salts and sodium sulphite, with an aniline of formula VI:

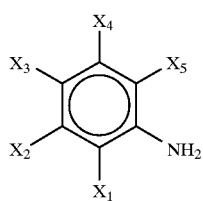

- or b) (G. M. Rubottom et al., J. Org. Chem., 1983, 48, 1550–1552) by reaction of methyllithium, and then of trimethylsilyl chloride, with a benzoic acid of formula VII:

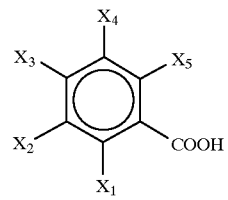

Certain benzoic acids of formula VII can also be prepared, in ways known per se, by ortholithiation of the corresponding benzene derivatives VIII:

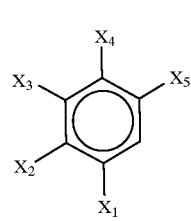

and treatment with solid carbon dioxide as described by V. Snieckus in Chem. Rev., 1990, 90, 879.

These acids can also be prepared by treating a benzoic acid of formula IX:

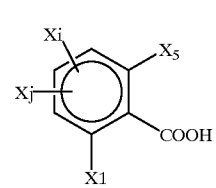

in which one of the Xi or Xj groups is a group capable of directing the metallation to the ortho position, with a strong lithiated base (alkyllithium compounds or lithium dialkylamides) and reaction with an electrophile, the metallation agent and the electrophile being described in the V. Snieckus reference above.

or c) by nitrous deamination of an acetophenone of formula V, in which $X_3$ is an amino, with an alkali metal nitrite or alkyl nitrite, preferably at 0° C., and then reacting the diazonium salt with a reducing agent such as hypophosphorous acid, an alcohol or an ether, preferably at a temperature of 0° C. to room temperature.

or d) by reaction of acetyl chloride with a substituted benzene of formula VI, in the presence of anhydrous aluminium chloride;

or e) by Fries rearrangement from an aryl acetate;

or f) by releasing the phenol functional group ($X_1$ is hydroxyl) from acetophenones of formula V, in which $X_1$ is an alkoxy or an alkylthio;

or g) by reaction of an acetophenone of formula V, in which at least one of the substituents X is a halogen atom, with a nitrogen-containing, oxygen-containing or sulphur-containing nucleophilic agent, preferably a thiolate in a preferably protic and non-polar solvent medium.

A second process known per se for the preparation of the derivatives of formula II according to the invention, in which Y is a bromine atom, consists in reacting a compound of formula II, in which I is a formyl group, with bromine in acetic acid to give the 4-bromo-3-phenylpyrazole.

A third process for the preparation of the derivatives of formula III, i.e, of formula II wherein Z is a hydrogen atom, according to the invention consists in reacting an enaminone of formula IV, in which W is a hydroxyl, alkoxy, alkylthio, alkylsulphinyl or -sulphonyl or halogen radical, an amino, mono- or dialkylamino or phenylamino group or a halogen and in which $X_1$, $X_2$, $X_3$, $X_4$ and $X_5$ have the same meanings as above and Y is halogen or cyano, with hydrazine hydrate at a temperature of 10° C. to 150° C., preferably of 20° C. to 120° C., advantageously in an organic solvent medium, preferably a lower carboxylic acid or in an alcohol, in the presence of an organic or inorganic acidic catalyst, the molar ratio of the two reactants being substantially stoechiometric.

The compounds of formula IV, for which Y is a halogen atom or a cyano group, W is a dialkylamino group and $X_1$, $X_2$, $X_3$, $X_4$ and $X_5$ being defined as above, can be obtained by reaction of acetophenones of formula V, in which $X_1$ to $X_5$ are defined as above and Y is a halogen atom or a cyano, with amide acetals, ester aminals or orthoaminals, in the absence of an organic solvent with dialkyl (preferably dimethyl or diethyl) acetals of N,N-dimethylformamide, or in an inert organic solvent medium such as toluene, cyclohexane, hexane, heptane or tetrahydrofuran, at a temperature of 10° C. to 50° C. and preferably of 15° C. to 40° C.

The derivatives of formula V can be prepared, in a way known per se, by reaction of a haloacetyl chloride with a substituted benzene of formula VI in the presence of anhydrous aluminium chloride.

The compounds of formula IV for which Y is halogen can also be obtained, in a way known per se, by reaction of an N-halosuccinimide in a chlorinated solvent with the compounds of formula IV for which Y is hydrogen.

A fourth process for the preparation of the compounds II consists in reacting a compound of formula II, in which at least one of the groups X is halogen, with a nitrogen-containing or oxygen-containing or sulphur-containing nucleophile, preferably a thiolate, in a preferably protic and non-polar solvent medium.

A fifth process for the preparation of the compounds II consists in reacting a compound of formula II, in which at least one of the groups X is alkylthio, with an oxidising agent such as hydrogen peroxide or the organic or inorganic peracids, preferably a persulphate, in a preferably protic and non-polar solvent medium.

The following examples are given by way of indication in order to illustrate the preparation and the fungicidal activity of the derivatives according to the invention. The structure of these derivatives has been confirmed by NMR analysis.

EXAMPLE 1

3',5'-dichloroacetophenone.

300 ml of water and 70 ml of concentrated hydrochloric acid are added to 48.6 g (0.30 mol) of 3,5-dichloroaniline. Then, after 30 minutes, 27.5 g (0.40 mol) of sodium nitrite in 32 ml of water are run in dropwise while maintaining the temperature between 0° C. and 5° C. 16.2 g (0.2 mol) of sodium acetate are added to the filtered reaction mixture. This solution is run in dropwise into a solution of 28.5 g (0.48 mol) of acetaldoxime, 25.0 g (0.10 mol) of copper sulphate pentahydrate, 20.5 g (0.018 mol) of anhydrous sodium sulphite and 121 g (1.50 mol) of sodium acetate in 250 ml of water maintained at 15° C. After stirring for 1 hour, the mixture is acidified by addition of concentrated hydrochloric acid. After steam distillation and chromatography of the crude product on a silica column (eluent 90/10 heptane/ethyl acetate), 16.6 g (yield 30 %) of 3', 5'-dichloroacetophenone (compound 1) are recovered in the form of a colourless liquid.

EXAMPLE 2

4-Acetyl-7-chloro-2,2-difluoro-1,3-benzodioxole (compound 2).

a) 7.5 g (0.038 mol) of 2,2-difluoro-1,3-benzodioxole-4-carboxylic acid, prepared according to the process described in European Application 0,333,658, are dissolved, with stirring and under an argon atmosphere, in 75 ml of dry tetrahydrofuran (THF). ml (0.081 mol) of n-butyllithium in solution in hexane are run in dropwise at –70° C. After stirring for 1 hour, 8.9 g (0.038 mol) of hexachloroethane in solution in 50 ml of dry tetrahydrofuran (THF) are run in. After 2 hours at –70° C., the temperature is allowed to return to 10° C. The reaction mixture is hydrolysed with 150 ml of ice-cold water and brought to a pH of approximately 1 by addition of 1N hydrochloric acid. The aqueous phase is extracted with ether, dried over magnesium sulphate and concentrated under vacuum. The solid is washed with heptane to give 3.7 g (0.016 mol) of 7-chloro-2,2-difluoro-1,3-benzodioxole-4-carboxylic acid (yield: 42%; melting point: 185° C.).

b) 3.7 g (0.016 mol) of 7-chloro-2,2-difluoro-1,3-benzodioxole-4-carboxylic acid obtained in a) dissolved in 100 ml of dry THF are reacted at 0° C., with stirring and under an argon atmosphere, with 30 ml (0.047 mol) of methyllithium in solution in ether. The reaction mixture is maintained for 2 hours at this temperature and then 29 ml (0.235 mol) of chloromethylsilane are rapidly added. The reaction mixture is allowed to return to room temperature and 130 ml of 1N hydrochloric acid are added. Stirring is maintained for 30 min at this temperature and the aqueous phase is then extracted with ether, dried over magnesium sulphate and concentrated under vacuum.

The residue is chromatographed on a silica column (eluent 90/10 heptane/ethyl acetate) to give 1.35 g (0.006 mol) of 4-acetyl-7-chloro-2,2-difluoro-1,3-benzodioxole (yield: 37%; melting point: 40° C.).

EXAMPLE 3 a) 29.0 g (0.200 mol) of 6-chloro-2-fluorotoluene are dissolved, with stirring, in 200 ml of dry THF. After cooling to –70° C., 151.0 ml (0.24 mol) of n-butyllithium in solution in hexane are added dropwise. After 2 hours, the reaction mixture maintained at –70° C. is poured onto solid carbon dioxide. After returning to room temperature, an aqueous ammonium chloride solution is added. The aqueous phase is extracted with ether, acidified with 6N hydrochloric acid and extracted with ether. The organic phases are dried over magnesium sulphate and concentrated to dryness. The residue is washed with heptane to give 9.0 g (0.048 mol) of 4-chloro-2-fluoro-3-methylbenzoic acid in the form of a white powder (yield: 24%; melting point: 198° C.).

b) By carrying out the reaction as in Example 2b, 1-acetyl-4-chloro-2-fluoro-3-methylbenzene (yield: 67%; melting point: 57° C.) is obtained (compound 3).

EXAMPLE 4

By carrying out the reaction as in Example 2, starting from the appropriately substituted acid, the derivatives of formula V and VII, collated in the following Table A, were obtained:

| COMPOUND No. | Stage | $X_1,X_2,X_3,X_4,X_5$ | Yld (%) | M.p. (° C.) or analysis |
|---|---|---|---|---|
| 4 | a | $OCF_2O,CH_3,H,H$ | 50 | 200° C. |
| 5 | b | $OCF_2O,CH_3,H,H$ | 73 | 60° C. |

EXAMPLE 4A (passing from VIII to VI) 2,4-Difluoro-3-chlorobenzoic acid (compound 47)

294 ml (0.471 mol) of a 1.6N solution of n-butyllithium in hexane are added dropwise and at −70° C. to a solution of 71 ml (0.471 mol) of tetramethylethylenediamine (TMEDA) in 300 ml of dry tetrahydrofuran (THF). 33.8 g (0.214 mol) of 2,4-difluorobenzoic acid, in 100 ml of dry tetrahydrofuran (THF), are added dropwise with stirring, under argon and at −70° C., to the above solution. After stirring for one hour, 111.5 g (0.471 mol) of hexachloroethane in solution in 150 ml of dry THF are run in. After two hours at −70° C., the temperature is allowed to return to 10° C. The reaction mixture is hydrolysed with 150 ml of ice-cooled water and brought to a pH of approximately 1 by addition of 3N hydrochloric acid. The aqueous phase is extracted with ether, dried over magnesium sulphate and concentrated. The residue is recrystallised from heptane/ether. 16.5 g (yield 40%) of 2,4-difluoro-3-chlorobenzoic acid are obtained.

By lithiation of the corresponding acids and then reaction with the appropriate reactant, the following acids were obtained.

| | $X_1, X_2, X_3, X_4, X_5$ | Yld (%) | M.p. (° C.) or analysis |
|---|---|---|---|
| 48 | Cl, Cl, F, H, H | 42 | 188 |
| 49 | $CH_3$, Cl, F, H, H | 59 | 186 |
| 50 | $OCF_2O$, $SCH_3$, H, H | 28 | 227 |
| 51 | $CH_3$, Cl, H, Cl, H | 85 | 160 |
| 52 | $OCF_2O$, Cl, H, H | 42 | 180 |
| 53 | $OCF_2O$, $CH_3$, H, H | 50 | 200 |

EXAMPLE 4B (passing from VII to VI) (compound 54)

29.0 g (0.2 mol) of 6-chloro-2-fluorotoluene are dissolved with stirring in 200 ml of dry THF. After cooling to −70° C., 151 ml (0.24 mol) of n-butyllithium in solution in hexane are added dropwise. After two hours, the reaction mixture, maintained at −70° C., is poured on solid carbon dioxide. After returning to room temperature, an aqueous ammonium chloride solution is added. The aqueous phase is extracted with ether, acidified with 6N hydrochloric acid and extracted with ether. The organic phases are dried over magnesium sulphate and concentrated to dryness. The residue is washed with heptane to give 9.0 g (0.048 mol) of 4-chloro-2-fluoro-3-methylbenzoic acid in the form of a white powder (yield: 24%; melting point: 198°)

EXAMPLE 4C (synthesis of VI from another VI via diazonium) 3-Bromo-2-chloro-5-methylbenzoic acid (compound 55)

The diazonium chloride of 2-amino-3-bromo-5-methylbenzoic acid is obtained by running an aqueous sodium nitrite solution (0.013 mol) dropwise at −5° C. onto a solution containing 0.0109 mol of 2-amino-3-bromo-5-methylbenzoic acid, 10 ml of hydrochloric acid, 10 ml of water and 30 ml of acetic acid. The reaction mixture is then stirred at 0° C. for 30 minutes and then poured into a large-volume round-bottomed flask containing 0.013 mol of cuprous chloride in 10 ml of acetic acid. The mixture obtained is brought to 60° C., stirred for 2 hours, and then hydrolysed after cooling by addition of ice. The precipitate obtained is filtered and washed with water. 3-Bromo-2-chloro-5-methylbenzoic acid is obtained: (Yield 58%, M.p. 160° C.).

The following compounds are obtained in the same way as above:

| COMPOUND NO. | $X_1, X_2, X_3, X_4, X_5$ | Yld (%) | M.p. (° C.) or analysis |
|---|---|---|---|
| 56 | Br, Br, H, $CH_3$, H | 70 | 145 |
| 57 | Br, $NO_2$, H, $CH_3$, H | 65 | |
| 58 | Cl, $NO_2$, H, $CH_3$, H | 69 | |
| 59 | Cl, Cl, H, Cl, H | 44 | 155 |
| 60 | $CH_3$, $NO_2$, H, Br, H | 75 | 175 |
| 61 | $CH_3$, $NO_2$, H, Cl, H | 56 | 138 |
| 62 | Cl, $CH_3$, H, $NO_2$, H | 78 | 203 |

EXAMPLE 4D (synthesis of acetophenones V from benzoic acids VI, T=Cl)

the acetophenones are obtained from the benzoic acids obtained above according to the following procedure:

a) 2,3-Dibromo-5-methylbenzoic acid chloride (compound 63).

2.1 g (0.00714 mol) of 2,3-dibromo-5-methylbenzoic acid in solution in 20 ml of 1,2-dichloroethane are treated by addition of 0.78 ml (0.107 mol) of thionyl chloride in solution in 5 ml of 1,2-dichloroethane. The mixture thus obtained is stirred at 60° C. for approximately 5 hours and then concentrated under vacuum to produce an oil: 2,3-dibromo-5-methylbenzoic acid chloride.

b) (2,3-dibromo-5-methylphenyl)ethanone (compound 64)

A mixture of 0.87 g (0.0076 mol) of magnesium ethoxide and 1.17 ml (0.0076 ml) of ethyl malonate is maintained at reflux in 30 ml of ether for 3 hours, 2 g (0.0064 mol) of the acid chloride obtained above, diluted in 5 ml of ether, are then added to this heterogeneous solution. The reaction mixture is then stirred at reflux for 3 hours. After cooling, 10 ml of a dilute sulphuric acid solution are added to the reaction mixture which is then extracted with ether and washed with water. After drying over $MgSO_4$ and evaporation of the solvent, there is obtained an oil which is used directly in the decarboxylation stage: dilution in a mixture of 5 ml of acetic acid, 5 ml of water and 1 ml of concentrated sulphuric acid and then heating at 70° C. for approximately 2 hours. The reaction mixture is then extracted with ethyl acetate and neutralised with an aqueous sodium hydroxide solution. After drying over $MgSO_4$ and evaporation of the solvent, an oil is obtained: (2,3-dibromo-5-methylphenyl) ethanone.

The following acetophenones are obtained in the same way as above from the appropriately substitued benzoic acids:

| COMPOUND NO. | $X_1, X_2, X_3, X_4, X_5$ | Yld (%) | M.p. (° C.) or analysis |
|---|---|---|---|
| 65 | Cl, $NO_2$, H, Cl, H | 93 | 64 |
| 66 | F, Cl, F, H, H | 73 | NMR |
| 67 | $OCF_2O$, $SCH_3$, H, H | 63 | 76 |
| 68 | $CH_3$, Cl, F, H, H | 23 | NMR |
| 69 | Cl, Cl, F, H, H | 83 | NMR |
| 70 | $NO_2$, H, Cl, H, H | 88 | 56 |
| 71 | $NO_2$, H, H, Cl, H | 58 | 62 |
| 72 | Cl, H, Cl, $CH_3$, H | 58 | B.p.$_{15}$:139 |
| 73 | $CH_3$, H, Cl, $CH_3$, H | 64 | 42 |
| 74 | $CH_3$, H, F, H, H | 45 | analysis |
| 75 | $NO_2$, H, $NO_2$, H, H | 75 | analysis |
| 76 | $CH_3$, H, H, H, $CH_3$ | 83 | analysis |
| 77 | Br, H, H, $NO_2$, H | 54 | analysis |
| 78 | $NO_2$, H, H, $CH_3$, H | 65 | analysis |
| 79 | H, Cl, F, Cl, H | 75 | analysis |
| 80 | Cl, Cl, H, Cl, H | 95* | NMR |
| 81 | $CH_3$, $NO_2$, H, Br, H | 80* | 80 |
| 82 | $CH_3$, $NO_2$, H, Cl, H | 43* | NMR |
| 83 | $CH_3$, Cl, H, Cl, H | 37* | NMR |
| 84 | $NO_2$, $CH_3$, H, $CH_3$, H | 67* | 68 |
| 85 | $CH_3$, $NO_2$, H, $CH_3$, H | 42* | NMR |
| 86 | Cl, $CH_3$, H, $NO_2$, H | 61* | 74 |

*decarboxylation is carried out by heating in a DMSO/water mixture.

EXAMPLE 4E
(synthesis of acetophenones V from benzoic acids VI, T=OH)

4-Acetyl-7-chloro-2,2-difluoro-1,3-benzodioxole (compound 87).

3.7 g (0.016 mol) of 7-chloro-2,2-difluoro-1,3-benxodioxolecarboxylic acid, dissolved in 100 ml of dry THF, are reacted at 0° C., with stirring and under an argon atmosphere, with 30 mol (0.047 mol) of methyllithium in solution in ether. The reaction mixture is maintained for two hours at this temperature and then 29 ml (0.0235 mol) of chlorotrimethylsilane are quickly added. The reaction mixture is left to return to room temperature and 130 ml of 1N hydrochloric acid are added. Stirring is maintained for 30 min at this temperature, and then the aqueous phase is extracted with ether, the ether extract is dried over magnesium sulphate and concentrated under vacuum. The residue is chromatographed on a silica column (eluent heptane/ethyl acetate 90/10) to give 1.35 g (0.006 mol) of 4-acetyl-7-chloro-2,2-difluro-1,3-benzodioxole (yield: 37%; melting point: 40° C.).

By carrying out the reaction as above, the following benzoic acids are obtained:

| COMPOUND NO. | $X_1, X_2, X_3, X_4, X_5$ | Yld (%) | M.p. (° C.) or analysis |
|---|---|---|---|
| 88 | F, $CH_3$, Cl, H, H | 67 | 57 |
| 89 | $OCF_2O$, $CH_3$, H, H | 73 | 60 |

EXAMPLE 4F
preparation of (3,5-dichlorophenyl)ethanone (compound 90)
a) from 3,5-dichloroaniline (passing from IV to V):

300 ml of water and 70 ml of concentrated hydrochloric acid are added to 48.6 g (0.30 mol) of 3,5-dichloroaniline. 30 minutes after, 27.5 g (0.40 mol) of sodium nitrite in 32 ml of water are run in dropwise while maintaining the temperature between 0° and 5° C. 16.2 g (0.2 mol) of sodium acetate are added to the filtered reaction mixture. This solution is run in dropwise onto a solution of 28.5 g (0.48 mol) of acetaldoxime, 25.0 g (0.10 mol) of copper sulphate pentahydrate, 20.5 g (0.018 mol) of anhydrous sodium sulphite and 121 g (1.50 mol) of sodium acetate in 250 ml of water maintained at 15° C. After stirring for 1 h, the mixture is acidified by addition of concentrated hydrochloric acid. After steam distillation and chromatography of the crude product on a silica column (heptane 90, ethyl acetate 10), there are recovered 16.6 g (30%) of (3,5-dichlorophenyl)-ethanone in the form of a colourless liquid.

By carrying out the reaction as above, from 3-bromo-5-trifluoromethylaniline, (3-bromo-5-trifluoromethylphenyl)ethanone (yield: 35%; melting point: NMR) is obtained.

b) from 4-acetyl-2,6-dichloroaniline (passing from V, $X_3=NH_2$ to V, $X_3=H$):

814 g (4 mol) of 4-acetyl-2,6-dichloroaniline, prepared according to patent DD 273,435 of the 15/11/1989, are recrystallised from a mixture of 1200 ml of concentrated hydrochloric acid and 5200 ml of concentrated acetic acid. After cooling to 0° C., a solution of 290 g (4.2 mol) of sodium nitrite in 770 ml of water is run in in a thin stream. After 2 h 30 at this temperature, the solution is run onto 2200 ml of a 50% solution of hypophosphorous acid in water at 5° C. At the end of the addition, the mixture is left to return to room temperature, 10 l of water are then added and the aqueous phase is extracted with dichloromethane. After drying of the separated organic phase, and concentration and distillation of the crude product, there are obtained 591 g (yield 70%, boiling point: 91–95° C. at 1 mm Hg) of (3,5-dichloro)phenyl-ethanone in the form of a pale yellow liquid.

By carrying out the reaction as above, from 4-acetyl-6-bromo-2-chloroaniline, there is obtained 89% of (3-bromo-5-chloro)phenylethanone (compound 91).

EXAMPLE 4G
(2-methoxy-3,5-dimethyl)phenylethanone: (passing from X to V):

a) (2,4-dimethyl)phenyl acetate (compound 92)

83 ml (1.02 mol) of pyridine are added to a solution of 120 ml (1 mol) of 2,4-dimethylphenol in 400 ml of dichloromethane cooled to 5° C. After stirring for 15 minutes and cooling the reaction mixture to −10° C., 73 ml (1.02 mol) of acetyl chloride in solution in 100 ml of dichloromethane are added dropwise. The reaction mixture is then brought to reflux for 2 hours, then cooled and treated by the addition of 200 ml of water, and then acidified to a pH of 1. The organic phase is extracted, dried over $MgSO_4$ and filtered on a silica bed, to lead to the production of a yellow oil: 2,4-dimethylphenyl acetate: yield 98%.

b) 2-acetyl-4,6-dimethylphenol (compound 93)

307 g (2.7 mol) of aluminium chloride are added progressively in portions to 160 g (0.97 mol) of (2,4-dimethyl)phenyl acetate obtained above and placed in a 1 litre, three-necked flask. The reaction mixture is brought progressively to 130° C. for 2 hours and then poured carefully, still hot, into a solution containing 2 litres of water and ice. Hydrolysis is completed by acidification of the solution to a pH of 2. The precipitate obtained is filtered on sintered glass and then recrystallised from heptane to lead to the production of an orangey powder: 2,5-dimethyl-6-acetylphenol: yield 55%.

c) (2-methoxy-3,5-dimethylphenyl)ethanone (passing from V, $X_1=OH$ to V, $X_1=OMe$) (compound 94)

16.4 g (0.1 mol) of the 2,4-dimethyl-6-acetylphenol obtained above are dissolved in 100 ml of acetone and treated by the addition of 13.8 g (0.1 mol) of $K_2CO_3$ and 10.4 ml (0.11 mol) of dimethyl sulphate. The reaction mixture is maintained at reflux for 14 hours and then, after cooling, 300 ml of water are added and the mixture is then extracted with dichloromethane. After drying the organic phase over MgSO$_4$ and evaporation, the residue obtained is purified by passing through a silica column (heptane/ethyl acetate 1/1) to lead to the production of an oil: (2-methoxy-3,5-dimethylphenyl)ethanone used crude.

(2-Methoxy-3,5-dichlorophenyl)ethanone (yield 78%, NMR), as well as (4-ethoxy-3-chlorophenyl)ethanone (compound 95), are obtained in the same way.

EXAMPLE 4H
(2-difluoromethoxy-3,5-dimethylphenyl)ethanone (compound 96) (passing from V, X$_1$=OH to V, X$_1$=OCHF$_2$)

10 ml of a 30% aqueous sodium hydroxide solution and 8.5 g (0.025 mol) of tetrabutylammonium hydrogensulphate are added to a solution of 8.2 g (0.05 mol) of 2-acetyl-4,6-dimethylphenol, obtained above in Example XXX, in dichloromethane. A stream of chlorodifluoromethane is then passed into the reaction mixture for 30 minutes and the latter is then stirred at room temperature for 4 hours. The reaction mixture is then extracted with dichloromethane and the extract is washed with water. After drying the organic phase over MgSO$_4$ and evaporation, the residue obtained is purified by passing through a silica column (dichloromethane) to lead to the production of a liquid: (2-difluoromethoxy-3,5-dimethylphenyl)ethanone: yield 21%.

EXAMPLE 4I
(preparation of chloroacetophenone V by chloroacetylation (Friedel-Crafts) of VII)

2-Chloro-1-(2-chloro-4-fluoro-5-methylphenyl)ethanone (compound 97).

14.1 g (0.125 mol) of monochloroacetyl chloride are run dropwise into a suspension of 16.66 g (0.125 mol) of anhydrous aluminium chloride in 100 ml of dry 1,2-dichloroethane maintained at a temperature of −5° C. by an ice/acetone bath. 14.46 g (0.1 mol) of 4-chloro-2-fluorotoluene are then run dropwise at the same temperature into the solution obtained. The reaction mixture is stirred for 1 hour at −5° C., then allowed to stand overnight and finally brought to 60° C. until gaseous evolution has ceased. After cooling with an ice bath, a solution of 5 ml of concentrated hydrochloric acid in 100 ml of water is run in dropwise. After separation, the organic phase is washed successively with 50 ml of water, 50 ml of saturated NaECO$_3$ solution and 50 ml of water, and then dried over anhydrous magnesium sulphate. After evaporation of the solvent, there are obtained 22.3 g of a pale-yellow oil of 2-chloro-1-(2-chloro-4-fluoro-5-methylphenyl)ethanone which crystallises on cooling (melting point: 32° C.; yield: 100%).

By using the same conditions and by replacing chloroacetyl chloride with acetyl chloride, the following acetophenones are obtained:

| COMPOUND NO. | X$_1$, X$_2$, X$_3$, X$_4$, X$_5$ | Yld (%) | M.p. (° C.) or analysis |
|---|---|---|---|
| 98 | Cl, H, Cl, CH$_3$, H | 58 | B.p.$_{15}$:139 |
| 99 | CH$_3$, H, Cl, CH$_3$, H | 64 | 42 |
| 100 | CH$_3$, H, F, H, H | 45 | analysis |
| 101 | CH$_3$, Br, CH$_3$, H, H | 23 | NMR |

EXAMPLE 5
1-(3,5-dichlorophenyl)-3-dimethylamino-2-propen-1-one (derivative 6).

10 g (0.053 mol) of 3', 5'-dichloroacetophenone are dissolved, at room temperature and with stirring, in 50 ml of N,N-dimethylformamide dimethyl acetal. Stirring is maintained and the reaction mixture is heated for 2 h at 90° C. The mixture is concentrated to dryness under reduced pressure. The residue is taken up in 150 ml of heptane. The orange residue is filtered to give 10.0 g (yield 77%, melting point: 100° C.) of 1-(3,5-dichlorophenyl)-3-dimethylamino-2-propen-1-one.

EXAMPLE 6

The reaction is carried out as in Example 5, starting from the appropriately substituted acetophenone and the appropriate second reactant.

The enaminone derivatives of formula IV in which W is the dimethylamino group, collated in Table B, were obtained.

| COMPOUND No. | X$^1$,X$^2$,X$^3$,X$^4$,X$^5$ | Yld (%) | M.p. (° C.) or analysis |
|---|---|---|---|
| 7 | H,H,Cl,H,H | 66 | 88° C. |
| 8 | Cl,H,Cl,H,H | 87 | 86° C. |
| 9 | H,Cl,Cl,H,H | 73 | 96° C. |
| 10 | Cl,H,H,Cl,H | 83 | 76° C. |
| 11 | H,H,OCH$_2$O,H | 44 | 125° C. |
| 12 | Cl,H,H,H,Cl | 70 | 106° C. |
| 13 | Cl,Cl,Cl,H,H | 74 | 98° C. |
| 14 | H,F,F,H,H | 79 | 62° C. |
| 15 | OCF$_2$O,CH$_3$,H,H | 61 | 126° C. |
| 16 | OCF$_2$O,Cl,H,H | 79 | 123° C. |
| 17 | F,CH$_3$,Cl,H,H | 84 | 95° C. |
| 102 | F, Cl, F, H, H | 63 | NMR |
| 103 | Cl, NO$_2$, H, Cl, H | 19 | 129 |
| 104 | Cl, Cl, F, H, H | 91 | 122 |
| 105 | F, F, F, H, H | 91 | 110 |
| 106 | H, Cl, Cl, Cl, H | 85 | 143 |
| 107 | CH$_3$, Br, CH$_3$, H, H | 68 | 79 |
| 108 | H, OCH$_3$, OCH$_3$, OCH$_3$, H | 88 | 126 |
| 109 | H, Cl, H, CH$_3$, H | 91 | crude |
| 110 | CH$_3$, Cl, F, H, H | 77 | 106 |
| 111 | NO$_2$, H, Cl, H, H | 91 | 147 |
| 112 | CH$_3$, H, CH$_3$, H, CH$_3$ | 42 | analysis |
| 113 | NO$_2$, H, H, Cl, H | 87 | 159 |
| 114 | Cl, H, Cl, CH$_3$, H | 88 | 114 |
| 115 | NO$_2$, H, CF$_3$, H, H | 75 | analysis |
| 116 | CH$_3$, H, Cl, CH$_3$, H | 68 | 92 |
| 117 | CH$_3$, H, F, H, H | 81 | 61 |
| 118 | CH$_3$, H, CH$_3$, H, H | 77 | analysis |
| 119 | NO$_2$, H, NO$_2$, H, H | 95 | analysis |
| 120 | CH$_3$, H, H, H, CH$_3$ | 87 | analysis |
| 121 | Br, H, H, NO$_2$, H | 76 | analysis |
| 122 | NO$_2$, H, H, CH$_3$, H | 82 | analysis |
| 123 | H, H, F, H, H | 76 | 84 |
| 124 | H, Cl, F, Cl, H | 86 | analysis |
| 125 | H, H, Cl, H, H | 66 | 88 |
| 126 | Cl, H, Cl, H, H | 87 | 86 |
| 127 | H, Cl, Cl, H, H | 73 | 96 |
| 128 | Cl; H; H, Cl, H | 83 | 76 |
| 129 | Cl, H, H, H, Cl | 70 | 106 |
| 130 | H, H, OCH$_2$O, H | 44 | 125 |
| 131 | OCF$_2$O, CH$_3$, H, H | 61 | 126 |
| 132 | F, CH$_3$, Cl, H, H | 84 | 95 |
| 133 | H, CH$_3$, H, CH$_3$, H | 74 | 88 |
| 134 | H, CF$_3$, H, CF$_3$, H | 82 | NMR |
| 135 | H, Br, H, CF$_3$, H | 75 | 99 |
| 136 | H, Br, H, Br, H | 72 | 111 |
| 137 | H, F, H, F, H | 90 | 114 |
| 138 | H, F, H, CF$_3$, H | 66 | 98 |
| 139 | OCF$_2$O, SCH$_3$, H, H | 88 | 104 |
| 140 | H, Br, F, H, H | 93 | 76 |
| 141 | H, Br, F, H, H | 93 | 76 |
| 142 | H, OCF$_3$, H, H, H | 95 | NMR |
| 143 | H, Cl, OEt, H, H | 99 | 142 |
| 144 | H, Cl, F, H, H | 83 | 71 |
| 145 | H, Cl, H, NO$_2$, H | 89 | 141 |
| 146 | H, Cl, H, Br, H | 94 | 103 |
| 147 | H, NO$_2$, H, NO$_2$, H | 56 | 197 |

EXAMPLE 7

3-(3,5-dichlorophenyl)-1H-pyrazole (derivative 18).

2.4 g (0.05 mol) of hydrazine hydrate are added slowly and at room temperature to a solution of 9 g (0.0369 mol) of 1-(3,5-dichlorophenyl)-3-dimethylamino-2-propen-1-one in 100 ml of ethanol. The reaction mixture is stirred for 2 hours at room temperature and then concentrated to dryness. The residue of triturated in heptane. 7.1 g (90% yield, melting point 156° C.) of 3-(3,5-dichlorophenyl)-1H-pyrazole are obtained.

EXAMPLE 8

By carrying out the reaction as in Example 7, except for compound 24 obtained in acetic acid at reflux, by starting from the appropriately substituted enaminone, the pyrazole derivatives, unsubstituted at position 4, of formula III collated in the following Table C were obtained:

| COMPOUND No. | $X_1, X_2, X_3, X_4, X_5$ | Yld (%) | M.p. (° C.) or analysis |
|---|---|---|---|
| 19 | H,H,Cl,H,H | 91 | 100° C. |
| 20 | Cl,H,Cl,H,H | 78 | 140° C. |
| 21 | H,Cl,Cl,H,H | 69 | 138° C. |
| 22 | Cl,H,H,Cl,H | 84 | 147° C. |
| 23 | H,OCH$_2$O,H,H | 87 | 124° C. |
| 24 | Cl,H,H,H,Cl | 100 | 167° C. |
| 25 | Cl,Cl,Cl,H,H | 91 | 164° C. |
| 26 | H,OCH$_3$,OCH$_3$,H,H | 88 | 125° C. |
| 27 | OCH$_3$,OCH$_3$,OCH$_3$,H | 72 | 125° C. |
| 28 | OCF$_2$O,CH$_3$,H,H | 87 | 140° C. |
| 29 | OCF$_2$O,Cl,H,H | 94 | 162° C. |
| 30 | F,CH$_3$,H,H,H | 77 | 90° C. |
| 148 | CH$_3$,Cl,F,H,H | 96 | 92 |
| 149 | H,Cl,F,Cl,H | 89 | 193 |
| 150 | H, OCH$_3$, OCH$_3$, OCH$_3$, H | 100 | NMR |
| 151 | H,Cl,Cl,Cl,H | 69 | 208 |
| 152 | H,CH$_3$,H,CH$_3$,H | 100 | NMR |
| 153 | H,CF$_3$,H,CF$_3$,H | 78 | 156 |
| 154 | H,Br,H,CF$_3$,H | 73 | 139 |
| 155 | Cl,NO$_2$,H,Cl,H | 85 | 106 |
| 156 | H,Br,H,Br,H | 68 | 162 |
| 157 | H,F,H,F,H | 90 | 128 |
| 158 | H,OCH$_3$,H,OCH$_3$,H | 97 | 109 |
| 159 | Cl,OCH$_3$,H,OCH$_3$,H | 77 | 129 |
| 160 | H, F, H, CF$_3$, H | 82 | 96 |
| 161 | OH,Cl,H,Cl,H | 72 | 206 |
| 162 | OCF$_2$O,SCH$_3$,H,H | 62 | 169 |
| 163 | H,Br,F,H,H | 88 | 115 |
| 164 | NO$_2$,H,Cl,H,H | 90 | 116 |
| 165 | NO$_2$,H,H,Cl,H | 27 | 125 |
| 166 | CH$_3$,H,CH$_3$,H,CH$_3$ | 80 | 189 |
| 167 | CH$_3$,H,CH$_3$,H,H | 74 | 86 |
| 168 | Cl,H,Cl,CH$_3$,H | 80 | 109 |
| 169 | CH$_3$,H,Cl,CH$_3$,H | 91 | 71 |
| 170 | Cl,Cl,F,H,H | 77 | 139 |
| 171 | CH$_3$,H,F,H,H | 94 | 51 |
| 172 | NO$_2$,H,NO$_2$,H,H | 75 | 150 |
| 173 | NO$_2$,H,H,CH$_3$,H | 95 | honeylike substance |
| 174 | CH$_3$,H,H,H,CH$_3$ | 21 | 176 |
| 175 | Br,H,H,NO$_2$,H | 71 | 174 |
| 176 | NO$_2$,H,CF$_3$,H,H | 91 | 99 |
| 177 | H,Cl,OEt,H,H | 87 | 121 |
| 178 | H,Cl,F,H,H | 41 | 111 |
| 179 | H,Cl,H,NO$_2$,H | 100 | 146 |
| 180 | H,Cl,H,Br,H | 83 | 150 |
| 181 | CH$_3$O,CH$_3$,H,CH$_3$O, H | 50 | 106 |
| 182 | H,H,F,H,H | | |
| | H,Br,H,CH$_3$,H | 90 | 101 |
| 183 | | 87 | 87 |
| 184 | F,F,F,H,H | 97 | 106 |
| 185 | Br,NO$_2$,H,CH$_3$,H | 48 | 122 |
| 186 | H,NO$_2$,H,NO$_2$,H | 79 | 195 |
| 187 | F,CH$_3$,H,H,F | 75 | 70 |
| 188 | F,H,H,H,F | 87 | 84 |
| 189 | H,Br,H,SCH$_3$,H | 89 | 103 |
| 190 | H,Br,H, SCH(CH$_3$)$_2$,H | 74 | gum |
| 191 | H,Cl,H,SCH$_3$,H | 100 | 84 |
| 192 | H,Cl,H, SCH(CH$_3$)$_2$,H | 100 | gum |
| 193 | CH$_3$,Br,CH$_3$,H,H | 79 | 110 |
| 194 | Cl,OCH$_3$,OCH$_3$ OCH$_3$, H | 95 | 74 |
| 195 | H,F,H,SCH(CH$_3$)$_2$, H | 100 | gum |
| 196 | H,F,H,SCH$_3$,H | 64 | 82 |
| 197 | F,CH$_3$,H,H,Cl | 66 | 88 |
| 198 | F,Br,H,H,F | 68 | 90 |

EXAMPLE 9

Halogenation of pyrazoles a) 4-chloro-3-(3,5-dichlorophenyl)-1H-pyrazole (compound 31):

2.3 g (0.0152 mol) of 3-(3,5-dichlorophenyl)-1H-pyrazole are dissolved, at room temperature and with stirring, in 300 ml of dichloromethane. 2.07 g (0.016 mol) of N-chlorosuccinimide are then added and then stirring is continued for 4 days at room temperature. The reaction mixture is then concentrated and then chromatographed on a silica column (eluent 70/30 heptane/ethyl acetate). 1.4 g (yield: 57%, melting point: 192° C.) of 4-chloro-3-(3,5-dichlorophenyl)-1H-pyrazole are obtained.

b) 4-chloro-3-(4-chlorophenyl)-1H-pyrazole (compound 32):

1.0 g (0.006 mol) of 3-(4-chlorophenyl)-1H-pyrazole are dissolved, at room temperature and with stirring, in 20 ml of acetic acid. 0.5 g (0.007 mol) of chlorine is then introduced into the reaction mixture. The white precipitate formed is filtered, washed with water and heptane and then chromatographed on a silica column (eluent 70/30 heptane/ethyl acetate). 0.7 g (0.002 mol) (yield: 58%, melting point: 158° C.) of 4-chloro-3-(4-chlorophenyl)-1H-pyrazole is obtained.

c) 4-bromo-3-(4-chlorophenyl)-1H-pyrazole (compound 33):

1.5 g (0.0084 mol) of 3-(4-chlorophenyl)-1H-pyrazole, prepared in the above example (19), are dissolved, at room temperature and with stirring, in 25 ml of acetic acid. 1.6 g (0.01 mol) of bromine are then run in dropwise while maintaining the temperature below 30° C. Stirring is maintained for 30 hours 30 min and then the reaction mixture is poured into water. The precipitate is filtered and washed with water and heptane. 2.1 g (0.0084 mol) (yield: 100%; melting point: 143° C.) of 4-bromo-3-(4-chlorophenyl)-1H-pyrazole are obtained.

d) 4-chloro-3-(3,5-dibromophenyl)pyrazole (compound 199):

4 g (0.0132 mol) of 3-(3,5-dibromophenyl)pyrazole and 1 g of pyridine (0.0132 mol) are dissolved, at room temperature and with stirring, in 50 ml of 1,2-dichloroethane. 2 g (0.0145 mol) of sulphuryl chloride in 10 ml of 1,2-dichloroethane are then added dropwise at 50° C. and stirring is then continued for 30 min days at this temperature. After cooling, the precipitate is filtered and recrystallised from 200 ml of 1,2-dichloroethane. 2.9 g (yield: 66%; melting point: 188° C.) of 4-chloro-3-(3,5-dibromophenyl) pyrazole are obtained.

e) 4-iodo-3-(3,5-dichlorophenyl)pyrazole (compound 200):

2.13 g (0.01 mol) of 3-(3,5-dichlorophenyl)pyrazole are dissolved, at room temperature and with stirring, in 50 ml of dichloromethane. 2.5 g (0.011 mol) of n-iodosuccinimide are then added and stirring is then continued for 4 days. The reaction mixture is then concentrated, the solid obtained is washed with heptane and boiled in 100 ml of 1N sodium hydroxide. After cooling, the solid is filtered, washed with water and dried to give 2 g (yield 59%, melting point: 170° C.) of 4-iodo-3-(3,5-dichlorophenyl)pyrazole.

EXAMPLE 10

By carrying out the reaction as in Example 9, starting from an appropriately substituted 3-phenyl-1H-pyrazole, the 3-phenyl-4-chloro or bromo)pyrazole derivatives of formula II, collated in the following Table D, were obtained:

| COMPOUND No. | $X_1,X_2,X_3,X_4,X_5$ | Y | Yld (%) | M.p. (° C.) or analysis |
|---|---|---|---|---|
| 34 | Cl,H,Cl,H,H | Br | 87 | 144° C. |
| 35 | H,Cl,Cl,H,H | Br | 100 | 159° C. |
| 36 | Cl,H,Cl,H,H | Cl | 86 | 144° C. |
| 37 | H,Cl,Cl,H,H | Cl | 69 | 154.5° C. |
| 38 | Cl,H,H,Cl,H | Cl | 53 | 140° C. |
| 39 | Cl,H,OCH$_2$O,H | Cl | 12 | 57° C. |
| 40 | H,H,OCH$_2$O,H | Cl | 8 | 140° C. |
| 41 | H,OCH$_3$,OCH$_3$,H,H | Cl | 86 | 148° C. |
| 42 | Cl,Cl,Cl,H,H | Cl | 58 | 194° C. |
| 43 | OCH$_3$,OCH$_3$,OCH$_3$,H | Cl | 43 | 110° C. |
| 44 | OCF$_2$O,CH$_3$,H,H | Cl | 58 | 170° C. |
| 45 | OCF$_2$O,Cl,H,H | Cl | 38 | 204° C. |
| 46 | F,CH$_3$,Cl,H,H | Cl | 77 | 131° C. |
| 201 | H,H,Cl,H,H | Br | 100 | 143 |
| 202 | H,CH$_3$,H,CH$_3$,H | Cl | 68 | 122 |
| 203 | H,CF$_3$,H,CF$_3$,H | Cl | 86 | 101 |
| 204 | H,Br,H,CF$_3$,H | Cl | 79 | 107 |
| 205 | H,Br,H,Br,H | Cl | 49 | 193 |
| 206 | H,F,H,F,H | Cl | 48 | 144 |
| 207 | Cl,NO$_2$,H,Cl | Cl | 71 | 158 |
| 208 | Cl,OCH$_3$,H,OCH$_3$,H | Cl | 37 | 218 |
| 209 | H,F,H,CF$_3$ | Cl | 57 | 57 |
| 210 | OCF$_2$O,SCH$_2$Cl,H,H | Cl | 1 | 161 |
| 211 | OCF$_2$O,SCH$_3$,H,H | Cl | 4 | 152 |
| 212 | K,Br,F,H,H | Cl | 86 | 144 |
| 213 | F,Cl,F,H,H, | Cl | 58 | 166 |
| 214 | NO$_2$,H,Cl,H,H | Cl | 36 | 189 |
| 215 | CH$_3$,H,CH$_3$,H,CH$_3$ | Cl | 20 | 148 |
| 216 | NO$_2$,H,H,Cl,H | Cl | 40 | 152 |
| 217 | Cl,H,Cl,CH$_3$,H | Cl | 34 | 182 |
| 218 | Cl,Cl,H,Cl,H | Cl | 59 | 135 |
| 219 | OCH$_3$,Cl,H,Cl,H | Cl | 50 | 124 |
| 220 | NO$_2$,H,CF$_3$,H,H | Cl | 48 | 168 |
| 221 | Cl,Cl,F,H,H | Cl | 76 | 181 |
| 222 | H,Cl,F,H,H | Cl | 63 | 145 |
| 223 | CH$_3$,H,Cl,CH$_3$,H | Cl | 74 | 97 |
| 224 | CH$_3$,H,F,H,H | Cl | 64 | honeylike substance |
| 225 | CH$_3$,Cl,F,H,H | Cl | 47 | 154 |
| 226 | CH$_3$,H,CH$_3$,H,H | Cl | 31 | honeylike substance |
| 227 | NO$_2$,H,NO$_2$,H,H | Cl | 7 | 167 |
| 228 | CH$_3$,H,H,H,CH$_3$ | Cl | 84 | 138 |
| 229 | Br,H,H,NO$_2$,H | Cl | 71 | 138 |
| 230 | NO$_2$,H,H,CH$_3$,H | Cl | 67 | honeylike substance |
| 231 | NO$_2$,H,F,Cl,H | Cl | 83 | 140 |
| 232 | NO$_2$,H,H,CF$_3$,H | Cl | 91 | 90 |
| 233 | NO$_2$,H,H,F,H | Cl | 80 | 93 |
| 234 | H,Cl,OH,NO$_2$,H | Cl | 66 | 161 |
| 235 | H,Cl,H,NO$_2$,H | Cl | 66 | 163 |
| 236 | H,Cl,NO$_2$,H,H | Cl | 8 | 153 |
| 237 | NO$_2$,H,F,Br,H | Cl | 70 | 154 |
| 238 | H,Cl,H,Cl,H | Br | 68 | 181 |
| 239 | H,Cl,H,Br,H | Cl | 89 | 188 |
| 240 | OCH$_3$,CH$_3$,H,CH$_3$,H | Cl | 63 | 130 |
| 241 | H,H,F,H,H | Cl | 17 | 147 |
| 242 | H,Br,H,CH$_3$,H | Cl | 82 | 180 |
| 243 | CH$_3$,NO$_2$,H,Br,H | Cl | 75 | 145 |
| 244 | CH$_3$,NO$_2$,H,Cl,H | Cl | 30 | 145 |
| 245 | F,F,F,H,H | Br | 86 | 123 |
| 246 | F,F,F,H,H | Cl | 29 | 143 |
| 247 | Br,NO$_2$,H,CH$_3$H | Cl | 50 | 187 |
| 248 | Br,Br,H,CH$_3$,H | Cl | 32 | 135 |
| 249 | H,NO$_2$,H,NO$_2$,H | Cl | 79 | 179 |
| 250 | Cl,Br,H,CH$_3$,H | Cl | 33 | 142 |
| 251 | OCHF$_2$,CH$_3$,H,CH$_3$,H | Cl | 20 | NMR |
| 252 | Cl,NO$_2$,H,CH$_3$,H | Cl | 66 | 194 |
| 253 | CH$_3$,Cl,H,Cl,H | Cl | 79 | 90 |
| 254 | NO$_2$,CH$_3$,H,CH$_3$,H | Cl | 24 | 160 |
| 255 | CH$_3$,NO$_2$,H,CH$_3$,H | Cl | 75 | 135 |
| 256 | Cl,H,F,CH$_3$,H | Cl | 70 | 133 |
| 257 | F,CH$_3$,H,H,F | Br | 100 | gum |
| 258 | F,H,H,H,F | Br | 50 | 142 |
| 259 | F,CH$_3$,H,H,F | Cl | 63 | 77 |
| 260 | F,H,H,H,F | Cl | 66 | 116 |
| 261 | H,Br,H,SCH$_3$,E | Br | 40 | 145 |
| 262 | H,Br,H,SCH(CH$_3$)$_2$,H | Br | 19 | gum |
| 263 | H,Cl,H,SCH$_3$,H | Br | 41 | 130 |
| 264 | H,Cl,H,SCH$_3$,H | Cl | 42 | 130 |
| 265 | H,Cl,H,SCH(CH$_3$)2,H | Br | 63 | gum |
| 266 | H,Cl,F,Cl,H | Cl | 60 | 167 |
| 267 | H,Cl,Cl,Cl,H | Cl | 61 | 208 |
| 268 | CH$_3$,Br,CH$_3$,H,H | Cl | 74 | 53 |
| 269 | CH$_3$,Br,CH$_3$,H,H | Br | 50 | 55 |
| 270 | H,OCH$_3$,OCH$_3$,OCH$_3$,H | Br | 70 | 176 |
| 271 | H,Cl,H,CH$_3$,H | Cl | 85 | 175 |
| 272 | H,Br,H,SCH$_3$,H | Cl | 65 | 120 |
| 273 | H,Br,H,SH,H | Cl | 25 | 175 |
| 274 | H,Cl,H,SH,H | Cl | 50 | 175 |
| 275 | H,F,H,SCH(CH$_3$)$_2$,H | Br | 81 | gum |
| 276 | F,NO$_2$,H,H,F | Cl | 52 | 67 |
| 276 | F,NO$_2$,H,CH$_3$,F | Cl | 73 | 171 |
| 277 | F,NO$_2$,H,CH$_3$,F | Br | 56 | 185 |
| 278 | F,CH$_3$,H,H,Cl | Br | 64 | 169 |
| 279 | F,CH$_3$,H,H,Cl | Cl | 78 | 156 |
| 280 | Cl,NO$_2$,H,CH$_3$, | Br | 59 | 177 |
| 281 | Cl,NO$_2$,H,CH$_3$,F | Cl | 42 | 167 |
| 282 | Cl,CH$_3$,H,NO$_2$,H | Cl | 45 | 183 |

EXAMPLE 11

The 3-(phenyl-4-chloro or bromo)pyrazole compounds of formula II, collated in the following Table E, are obtained by oxidation of the corresponding methylthio to the oxone in methanol.

| COMPOUND No. | $X_1,X_2,X_3,X_4,X_5$ | Y | Yld (%) | M.p.(° C.) or analysis |
|---|---|---|---|---|
| 283 | H,Br,H,SOCH$_3$,H | Br | 62 | gum |
| 284 | H,Br,H,SO$_2$CH$_3$,H | Br | 73 | 158 |
| 285 | H,Cl,H,SO$_2$CH$_3$,H | Cl | 40 | 170.5 |
| 286 | H,Cl,H,SOCH$_3$,H | Cl | 40 | 50 |
| 287 | H,Cl,H,SOCH$_3$,H | Br | 87 | gum |
| 288 | H,H,H,SOCH(CH$_3$)$_2$,H | Br | 67 | 60 |
| 289 | H,Br,H,SOCH$_3$,H | Cl | 71 | gum |
| 290 | H,Br,H,SO$_2$CH$_3$,H | Cl | 39 | 152 |

EXAMPLE 12

Production of a compound of formula II from another compound of formula II by nitration: (compound 291)

a) Acetylation:

0.25 g (0.005 mol) of 4-dimethylaminopyridine and 4.25 g (0.042 mol) of triethylamine are added to 11.0 g (0.046 mol) of 4-chloro,3-(2,2-difluorobenzo-1,3-dioxol-4-yl)-1H-pyrazole (prepared as described in patent PH 91-033) dissolved in 100 ml of THF. A solution of 3.6 g (0.046 mol) of acetyl chloride in 50 ml of THF is run dropwise and at 0° C. onto this solution. Stirring is continued for 3 h at room temperature. The reaction mixture is poured into 300 ml of water and extracted with ethyl acetate. After drying the organic phase and concentration under vacuum, the residue is triturated with 50 ml of heptane, filtered and dried. We obtain 12.8 g of 1-acetyl-4-chloro-3-(2,2-difluorobenzo-1,3-dioxol-4-yl)pyrazole melting at 131° C.

b) Nitration:

6.3 g (0.063 mol) of $KNO_3$ are added, in small portions and at 0° C., to 12.8 g of 1-(acetyl),4-chloro, 3-(2,2-difluorobenzo-1,3-dioxol-4-yl)pyrazole dissolved in 21 ml of $H_2SO_4$ (96%) and 140 ml of $CH_2Cl_2$. The reaction mixture is stirred for 3 h at 0° C. and then poured poured onto 300 cm$^3$ of ice. The precipitate is recovered by filtration, washed with water and then heptane and dried. We obtain 8.05 g of 4-chloro-3-(2,2-difluoro-5-nitrobenzo-1,3-dioxol-4-yl)pyrazole melting at 180° C. (yield 63%).

In the same way, 3-(3,5-dichloro)phenyl-4-chloropyrazole is nitrated to produce 3-(3,5-dichloro-2-nitrophenyl)-4-chloropyrazole (compound 292) (yield 55%, M.p. 173° C.) and 3-(3,5-dichloro-4-nitrophenyl)-4-chloropyrazole (yield 8%, M.p. 177° C.) (compound 293).

EXAMPLE 13

Production of a compound of formula II from another compound of formula II by reduction (compound 294)

6.0 g (0.02 mol) of 4-chloro-3-(2,2-difluoro-5-nitrobenzo-1,3-dioxol-4-yl)pyrazole, in solution in 60 ml of ethanol, are run, at room temperature, onto a mixture of 30 ml of 36% HCl and 20.2 g (0.09 mol) of $SnCl_2.2H_2O$ in 60 ml of ethanol. The reaction mixture is stirred for 2 h at room temperature, neutralised with 10% NaOH and then filtered. The insoluble material is washed with ethanol. The alcohol phase is concentrated under reduced pressure and the residue is taken up in ethyl acetate. After drying the organic phase and concentration under vacuum, the residue is triturated with 50 ml of heptane, filtered and dried. We obtain 4.6 g of 4-chloro,3-(5-amino,2,2-difluorobenzo-1,3-dioxol-4-yl) pyrazole melting at 195° C. (yield 84%).

The pyrazole 4-chloro-3-(3-amino-2,5-dimethylphenyl) pyrazole (compound 295) is obtained in an identical way (melting point 70° C.; yield 85%).

EXAMPLE 14

3-(2-amino-3 5-dichloro)phenyl-4-chloropyrazole (compound 296)

14.6 g (0.05 mol) of 3-(2-nitro-3,5-dichlorophenyl)-4-chloropyrazole, in solution in 200 ml of acetic acid, are introduced into a 500 ml, three-necked, round-bottomed flask. The solution is brought to 50° C. and 8.4 g (0.15 mol) of iron powder are introduced in portions. The reaction mixture is then kept stirring at 70° C. for 5 hours. After cooling, the reaction mixture is poured into 800 ml of water, filtered on sintered glass, rinsed with water and dried to lead to the production of a white solid (yield: 90%, M.p.: decomposition at 300° C.) of 3-(2-amino-3,5-dichlorophenyl)-4-chloropyrazole.

The pyrazole 4-chloro-3-(3-amino-5-chlorophenyl) pyrazole is obtained in an identical way (melting point 150° C., yield 41%) (compound 297). The pyrazole 4-chloro-3-(4-amino-3,5-dichlorophenyl)pyrazole (compound 298) is obtained in an identical way (melting point 217° C.; yield 82%).

EXAMPLE 15

3-(2-methylthio-3,5-dichloro)phenyl-4-chloropyrazole (compound 299)

This compound is obtained by diazotisation of 3-(2-amino-3,5-dichlorophenyl)-4-chloropyrazole, according to the methods described in the literature: yield 30%, honey-like consistency.

The 3-phenyl-4-chloro or bromo)pyrazole compounds of formula II, which are given below, are obtained by a similar process with the appropriate reactant:

| COMPOUND No. | $X_1,X_2,X_3,X_4,X_5$ | Y | Yld (%) | M.p.(° C.) or analysis |
|---|---|---|---|---|
| 300 | $OCF_2O$,H,Cl,H | Cl | 45 | 185 |
| 301 | $OCF_2O$,H,$SCH_3$,H | Cl | 60 | 188 |
| 302 | $OCF_2O$,H,Br,H | Cl | 19 | 218 |
| 303 | $CH_3$,OH,H,$CH_3$,H | Cl | 32 | 175 |
| 304 | Br,Cl,H,Cl,H | Cl | | |

EXAMPLE 16

Production of a compound of formula II from another compound of formula II by nucleophilic aromatic substitution 3-(5-Chloro-2-nitro-3-methylthio)phenyl-4-chloropyrazole (compound 305)

5.85 g (0.02 mol) of 3-(3,5-dichloro-2-nitrophenyl)-4-chloropyrazole obtained in Example No. xxx and 1.5 g (0.021 mol) of sodium methanethiolate in 50 ml of DMF are introduced into a 250 ml, three-necked, round-bottomed flask. The reaction mixture is heated at 50° C. for 1 hour, then hydrolysed with 200 ml of water and extracted with ethyl acetate. After drying over $MgSO_4$ and evaporation of the solvent, a yellow oil is obtained: yield 89%.

By a similar process, starting from 3-(3,5-dichlorophenyl)-4-chloropyrazole and 3 equivalents of sodium methanolate in NMP, 3-(3-chloro-5-mercaptophenyl)-4-chloropyrazole, melting point 175° C. (compound 306), is obtained with a yield of 50%.

EXAMPLE 17

Production of 4-halo-3-phenylpyrazole salts:

Hemihydrochloride of 4-chloro-3-(3,5-dichlorophenyl) pyrazole (compound 307):

2 g (0.008 mol) of 4-chloro-3-(3,5-dichlorophenyl) pyrazole are dissolved, at room temperature and with stirring, in 200 ml of diethyl ether. Sparging with hydrochloric acid is then carried out until precipitation has ended. The white solid is filtered and rinsed with ether to give 1.1 g (yield 52%, melting point: 175° C.) of 4-chloro-3-(3,5-dichlorophenyl)pyrazole hemihydrochloride.

By carrying out the reaction as in the above example, the following salts were obtained:

| COMPOUND No. | $X_1, X_2, X_3, X_4, X_5$ | Y | Z | Yld (%) | M.p.(° C.) or analysis |
|---|---|---|---|---|---|
| 308 | H,Cl,H,Cl,H; 1 HSO$_4$H | Cl | H | 58 | 195 |
| 309 | H,Cl,H,Cl,H; 1 HSO$_3$CH$_3$ | Cl | H | 18 | 110 |

EXAMPLES 18

Pyrazoles substituted in the 4 position by a substituent Y other than a halogen atom 18 A) 3-(4-Bromophenyl)-4-methylsulphonyl-pyrazole (compound 310)

47.7 g (0.15 mol) of 4-bromoacetophenone in solution in 500 ml of acetonitrile are added to 15.3 g (0.15 mol) of sodium methylsulphinate and maintained at reflux for 48 hours. After cooling and evaporation of the acetonitrile, the reaction mixture is washed with water and extracted with CH$_2$Cl$_2$. The crude residue obtained is purified by trituration in diisopropyl ether and leads to the production of a beige powder: yield 72%, M.p. 165° C.

8.3 g (0.03 mol) of (4-bromophenyl)methyl-sulphonylacetophenone are dissolved in 30 ml of N,N-dimethylformamide dimethyl acetal and heated at 70° C. according to the procedure described in Example No. 5, and then, after isolation of the intermediate enaminone, 2.85 ml (0.06 mol) of hydrazine hydrate are added according to the procedure described in Example No. 7. After purification by trituration in diisopropyl ether, a beige powder is obtained: yield: 88%, M.p. 70° C.

18 B) 3-(3,5-Dichlorophenyl)-4-methylthio-pyrazole (compound 311):

i) 2-Bromo-1-(3,5-dichlorophenyl)-1-ethanone:

1.03 ml (0.02 mol) of bromine are added, at room temperature, to 3.77 g (0.019 mol) of (3,5-dichlorophenyl)ethanone in solution in 50 ml of acetic acid. After stirring for 12 hours, evaporation of the acetic acid leads to the production of a yellow precipitate: 2-bromo-1-(3,5-dichlorophenyl)-1-ethanone (yield 81%).

ii) 1-(3,5-Dichlorophenyl)-2-methylthio-1-ethanone:

3.7 g (0.015 mol) of 1-(3,5-dichlorophenyl)-2-methylthio-1-ethanone are prepared by addition at 0° C. of 1.23 g (0.017 mol) of sodium methanethiolate in solution in 10 ml of methanol to 4.28 g (0.016 mol) of 2-bromo-1-(3,5-dichlorophenyl)-1-ethanone obtained above.

iii) 3-(3,5-Dichlorophenyl)-4-methylthio-pyrazole:

2.3 g (0.0098 mol) of 1-(3,5-dichlorophenyl)-2-methylthio-1-ethanone are dissolved in 4 ml (0.029 mol) of N,N-dimethylformamide dimethyl acetal and heated at 70° C. according to the procedure described in Example No. 5, and then, after isolation of the intermediate enaminone, 0.9 ml (0.019 mol) of hydrazine hydrate are added according to the procedure described in Example No. 7. After purification by trituration in heptane, 1.12 g of the desired compound are obtained: yield 44%, M.p. 148° C.

18 C) 3-(3,5-Dichlorophenyl)-4-methoxypyrazole (compound 312):

i) 1-(3,5-Dichlorophenyl)-2-methoxy-1-ethanone:

1-(3,5-Dichlorophenyl)-2-methoxy-1-ethanone is obtained by addition at 5° C. of 5.74 g (0.023 mol) of 3,5-dichlorophenylmagnesium bromide to a solution in 10 ml of THF of 1.77 ml (0.0213 mol) of methoxyacetonitrile. The mixture is stirred at room temperature for 2 hours and then hydrolysed by pouring it into an ice-cold solution of water and 1N hydrochloric acid. The aqueous phase is extracted with ethyl acetate and the organic phase is brought to a basic pH by washings with a saturated sodium bicarbonate solution. After drying over MgSO$_4$ and evaporation of the solvents, the oily residue obtained is purified by chromatography on silica gel (ethyl acetate/heptane 10/90).

ii) 3-(3,5-Dichlorophenyl)-4-methoxypyrazole:

0.47 g (0.0021 mol) of 1-(3,5-dichlorophenyl)-2-methoxy-1-ethanone thus obtained are dissolved in 1 ml (0.0074 mol) of N,N-dimethylformamide dimethyl acetal and heated at 70° C. according to the procedure described in Example No. 5, and then, after isolation of the intermediate enaminone, 0.12 ml (0.0024 mol) of hydrazine hydrate are added according to the procedure described in Example No. 7. After purification by trituration in heptane, 0.27 g of the desired compound are obtained: yield 52%, M.p. 173° C.

18 D) 3-(3,5-Dichloro)phenyl-4-dimethylamino-pyrazole (compound 313):

This compound is prepared by analogy with the procedure described in "Il Farmaco Ed. Sc.", 39, 618, 1983 by P. Giori et al., with 3,5-dichlorophenylacetonitrile as starting material. Yield 33%. Honey-like consistency.

18 E) Production of compounds of formula II by cyclisation between Y and X$_5$: 8-Bromo-4,5-dihydro-2H-benz[g] indazole (compound 314)

This compound is prepared from 1.66 g (0.0059 mol) of 6-bromo-2-(dimethylaminomethylene)-tetralone and 0.58 g (0.008 mol) of hydrazine hydrate in ethanol as described in Example 7: yield: 31%, melting point: 155° C.

EXAMPLES 19

Pyrazoles substituted in the 1 position by a substituent Z other than a hydrogen atom:

19 A) 1-Isopropylaminocarbonyl-4-chloro-3-(3,5-dichlorophenyl)pyrazole (compound 315):

0.95 g (0.011 mol) of isopropyl isocyanate are added, dropwise and at 0° C., to a solution of 2.55 g (0.01 mol) of 4-chloro-3-(3,5-dichlorophenyl)-1H-pyrazole and 1.55 ml (0.011 mol) of triethylamine in 20 ml of anhydrous DMF. Stirring is continued for 2 h at room temperature. The reaction mixture is poured into 100 ml of water and extracted with ethyl acetate. After drying the organic phase and concentration under vacuum, the residue is triturated with 50 ml of heptane, filtered and dried. We obtain 2.10 g of 1-isopropylaminocarbonyl-4-chloro-3-(3,5-dichlorophenyl)pyrazole, melting at 127° C.

19 B) 1-Acetyl-4-chloro-3-(3,5-dichlorophenyl)pyrazole (compound 316):

0.35 g (0.003 mol) of 4-dimethylaminopyridine and 1.55 ml (0.011 mol) of triethylamine are added to 2.55 g (0.01 mol) of 4-chloro-3-(3,5-dichlorophenyl)-pyrazole dissolved in 30 ml of THF. A solution of 0.85 g (0.011 mol) of acetyl chloride in 10 ml of THF is run, dropwise and at 0° C., onto this solution. Stirring is continued for 2 h at room temperature. The reaction mixture is poured into 100 ml of water and extracted with ethyl acetate. After drying the organic phase and concentration under vacuum, the residue is triturated with 50 ml of heptane, filtered and dried. We obtain 2.80 g of 1-acetyl-4-chloro-3-(3,5-dichlorophenyl)pyrazole, melting at 125° C.

19 C) 1-Methoxycarbonyl-4-chloro-3-(3,5-dichlorophenyl)pyrazole (compound 317):

2.52 g (0.0204 mol) of 4-dimethylaminopyridine and 18.3 ml (0.132 mol) of triethylamine are added to 30.55 g (0.12 mol) of 4-chloro-3-(3,5-dichlorophenyl)pyrazole dissolved in 300 ml of THF. A solution of 12.5 g (0.132 mol) of methyl chloroformate in 100 ml of THF is run, dropwise and at 0° C., into this solution. Stirring is continued for 20 h at room temperature. The reaction mixture is poured into 500 ml of water and extracted with ethyl acetate. After drying the organic phase and concentration under vacuum, the residue is triturated with 150 ml of heptane, filtered and dried. We obtain 33.5 g of 1-methoxycarbonyl-4-chloro-3-(3,5-dichlorophenyl)pyrazole, melting at 144° C.

The following 1-substituted-4-chloro-3-phenylpyrazole compounds are prepared as in Example 19 C:

| COMPOUND No. | $X_1,X_2,X_3,X_4,X_5$ | Y | Yld (%) | M.p.(° C.) or analysis |
|---|---|---|---|---|
| 318 | H,Cl,H,Cl,H | $CO_2Bn$ | 48 | 118 |
| 319 | H,Cl,H,Cl,H | $CO_2CH_2CH_2Cl$ | 60 | 108 |
| 320 | H,Cl,H,Cl,H | $CO_2C(CH_3)_2CCl_3$ | 75 | 135 |
| 321 | H,Cl,H,Cl,H | $CO_2Et$ | 50 | 112 |
| 322 | H,Cl,H,Cl,H | $CO_2All$ | 48 | 80 |

19 D) 1-Acetoxymethyl-4-chloro-3-(3,5-dichlorophenyl)pyrazole (compound 323):

0.15 ml of 1,8-diazabicyclo(5.4.0)undecen-7-ene is added, at room temperature, to a solution of 2.55 g (0.01 mol) of 4-chloro-3-(3,5-dichlorophenyl)pyrazole and 0.90 g (0.030 mol) of paraformaldehyde in 70 ml of THF. The reaction mixture is stirred for 4 h at room temperature. A solution of 1.20 g (0.015 mol) of acetyl chloride in 10 ml of THF is run in dropwise at 0° C. and stirring is continued for 6 h at room temperature. The reaction mixture is concentrated to dryness. The residue is taken up in 15 ml of heptane and then dried. We obtain 3.05 g of 1-acetoxymethyl-4-chloro-3-(3,5-dichlorophenyl)pyrazole, melting at 95° C.

19 E) 1-Chloromethyl-4-chloro-3-(3,5-dichlorophenyl)pyrazole (compound 324):

0.15 ml of 1,8-diazabicyclo(5.4.0)undecen-7-ene is added, at room temperature, to a solution of 2.55 g (0.01 mol) of 4-chloro-3-(3,5-dichlorophenyl)pyrazole and 0.90 g (0.030 mol) of paraformaldehyde in 70 ml of THF. The reaction mixture is stirred for 4 h at room temperature. A solution of 4.75 g (0.015 mol) of thionyl chloride in 20 ml of THF is run in dropwise at 0° C. Stirring is continued for 4 h at room temperature. The reaction mixture is concentrated to dryness. The residue is taken up in 15 ml of heptane and then dried. We obtain 2.15 g of 1-chloromethyl-4-chloro-3-(3,5-dichlorophenyl)pyrazole, melting at 88° C.

19 F) 1-Azidomethyl-4-chloro-3-(3,5-dichlorophenyl)pyrazole (compound 325):

0.70 g (0.010 mol) of sodium azide is added, at room temperature, to a solution of 1.85 g (0.005 mol) of 1-chloromethyl-4-chloro-3-(3,5-dichlorophenyl)pyrazole in 25 ml of DMF. The reaction mixture is stirred for 12 h, diluted with 100 ml of $H_2O$ and extracted with ether. After drying the organic phase and concentration under vacuum, the residue is triturated with 20 ml of heptane, filtered and dried. We obtain 1.30 g of 1-azidomethyl-4-chloro-3-(3,5-dichlorophenyl)pyrazole, melting at 74° C.

19 G) Chloride of 1-triphenylphosphonomethyl-4-chloro-3-(3,5-dichlorophenyl)pyrazole (compound 326):

1.85 g (0.005 mol) of 1-chloromethyl-4-chloro-3-(3,5-dichlorophenyl)pyrazole and 1.65 g (0.00625 mol) of triphenylphosphine in 30 ml of THF are maintained at reflux for 8 h (inert atmosphere). After returning to room temperature, the insoluble material is recovered by filtration, triturated with 15 ml of heptane, filtered and dried. We obtain 0.50 g of the chloride of 1-triphenylphosphonomethyl-4-chloro-3-(3,5-dichlorophenyl)pyrazole, which product decomposes at 260° C.

19 H) 1-t-Butoxycarbonylmethyl-4-chloro-3-(3,5-dichlorophenyl)pyrazole (compound 327):

A solution of 5.00 g (0.033 mol) of t-butyl chloroacetate in 30 ml of DMF is run, dropwise and at room temperature, into a mixture of 7.62 g (0.030 mol) of 4-chloro-3-(3,5-dichlorophenyl)pyrazole and 5.60 g (0.040 mol) of $K_2CO_3$. The reaction mixture is stirred for 12 h at room temperature, diluted with 200 ml of $H_2O$ and extracted with ether. After drying the organic phase and concentration under vacuum, the residue is triturated with 20 ml of heptane, filtered and dried. We obtain 10.20 g of 1-t-butoxycarbonylmethyl-4-chloro-3-(3,5-dichlorophenyl)pyrazole, melting at 86° C.

19 I) 1-Carboxymethyl-4-chloro-3-(3,5-dichlorophenyl)pyrazole (compound 328):

A solution of 6.85 g (0.0185 mol) of 1-t-butoxycarbonylmethyl-4-chloro-3-(3,5-dichlorophenyl)pyrazole in 100 ml of trifluoroacetic acid is stirred for 16 h at room temperature. The reaction mixture is poured onto 300 cm³ of an ice/water mixture. The insoluble material is recovered by filtration, washed with heptane and dried. We obtained 5.65 g of 1-carboxymethyl-4-chloro-3-(3,5-dichlorophenyl)pyrazole, melting at 182° C.

19 J) 1-Carboxymethyl-4-chloro-3-(3,5-dichlorophenyl)pyrazole (compound 329):

A solution of 3.25 g (0.010 mol) of 1-carboxymethyl-4-chloro-3-(3,5-dichlorophenyl)pyrazole and 0.80 g of sodium hydroxide pellets in 50 ml of ethanol is maintained at reflux for 1 h. After returning to room temperature, the insoluble material is recovered by filtration, triturated with 30 ml of heptane, filtered and dried. We obtain 2.65 g of the sodium salt of 1-carboxymethyl-4-chloro-3-(3,5-dichlorophenyl)pyrazole, melting at 246° C.

EXAMPLE 20

In vivo test on Botrytis cinerea on excised tomato leaf (strains sensitive and strains resistant to benzimidazoles)

An aqueous suspension of the active material to be tested, having the following composition, is prepared, by fine milling:

active material: 60 mg surface-active agent Tween 80 (oleate of polyoxyethylenated derivative of sorbitan) diluted to 10% in water: 0.3 ml made up to 60 ml with water.

This aqueous suspension is then diluted with water to obtain the desired concentration of active material.

Tomatoes cultivated under glass (variety Marmande), 30 days old, are treated by spraying with aqueous suspensions as defined above and at various concentrations of the test compound.

After 24 hours, the leaves are cut and put in a Petri dish (diameter 14 cm), the bottom of which has been covered beforehand with a wet filter paper disc (10 leaflets per dish).

The inoculum is then introduced, using a syringe, by deposition of drops (3 per leaflet) of a suspension of spores of *Botrytis cinerea*, which are sensitive to benzimidazoles or resistant to benzimidazoles, which suspension is obtained from 15-day cultures subsequently suspended at a concentration of 150,000 units per cm³.

Inspection is carried out 6 days after infection by comparison with an untreated control.

Under these conditions, at a dose of 1 g/l, a good (at least 75%) or total protection is observed with the following compounds: 20, 31, 45, 46, 199, 202, 204 to 207, 212, 213, 218, 219, 221, 222, 225, 234, 238, 239, 241 to 247, 250, 253 to 255, 296, 307, 316, 319, 321 and 322 against Botrytis sensitive to benzimidazoles.

EXAMPLE 21

In vivo test on Pyricularia oryzae responsible for piriculariosis in rice:

An aqueous suspension of the active material to be tested, having the following composition, is prepared, by fine milling:

active material: 60 mg surface-active agent Tween 80 (oleate of polyoxyethylenated derivative of sorbitan) diluted to 10% in water: 0.3 ml made up to 60 ml with water.

This aqueous suspension is then diluted with water to obtain the desired concentration of active material.

Rice, seeded in small pots in a 50/50 mixture of enriched peat and pozzolana, is treated at the 10 cm-high stage by spraying with the above aqueous suspension.

After 24 hours, an aqueous suspension of spores of Pyricularia oryzae, which suspension is obtained from a 15-day culture subsequently suspended at a concentration of 100,000 units per cm$^3$, is applied to the leaves.

The rice plants are incubated for 24 hours (25° C., 100% relative humidity) and are then put in an observation cell, under the same conditions, for 5 days.

Reading is carried out 6 days after infection.

Under these conditions, at a dose of 1 g/l, a good (at least 75%) or total protection is observed with the following compounds: 7, 20, 22, 31, 36, 37, 38, 42, 45, 46, 202 to 207, 209, 211 to 213, 218 to 226, 231, 238, 239, 241 to 246, 249, 250, 253 to 256, 293, 294, 301, 305, 316 to 318, 321.

EXAMPLE 22

In vivo test on Plasmopara viticola:

An aqueous suspension of the active material to be tested, having the following composition, is prepared, by fine milling:

active material: 60 mg surface-active agent Tween 80 (oleate of polyoxyethylenated derivative of sorbitan) diluted to 10% in water: 0.3 ml made up to 60 ml with water.

This aqueous suspension is then diluted with water to obtain the desired concentration of active material.

Vine (*Vitis vinifera*) cuttings, variety Chardonnay, are grown in small pots. When these plants are 2 months old (8- to 10-leaf stage, height of 10 to 15 cm), they are treated by spraying with the above aqueous suspension.

Seedlings, used as controls, are treated with an aqueous solution which does not contain the active material.

After drying for 24 hours, each seedling is infected by spraying with an aqueous suspension of spores of *Plasmopara viticola*, which suspension is obtained from a 7-day culture subsequently suspended at a concentration of 100, 000 units per cm$^3$.

The infected seedlings are then incubated for two days at approximately 18° C., in an atmosphere saturated with moisture, and then for 5 days at approximately 20–22° C. at 90–100% relative humidity.

Reading is carried out 7 days after infection, in comparison with the control seedlings.

Under these conditions, at a dose of 1 g/l, a good (at least 75%) or total protection is observed with the following compounds: 20, 21, 25, 31, 33, 34, 36, 37, 41, 43, 200 to 204, 206, 207, 212, 213, 219 to 221, 223 to 228, 230, 231, 234, 236 to 239, 243 to 245, 248, 254 to 256, 291, 294, 305, 307 and 313.

EXAMPLE 23

In vivo test on Puccinia recondita (wheat brown rust):

An aqueous suspension of the active material to be tested, having the following composition, is prepared, by fine milling:

active material: 60 mg surface-active agent Tween 80 (oleate of polyoxyethylenated derivative of sorbitan) diluted to 10% in water: 0.3 ml made up to 60 ml with water to obtain a 1 g/l suspension/solution.

This aqueous suspension is then optionally diluted with water to obtain the desired concentration of active material.

Wheat, in small pots, seeded on a 50/50 peat/pozzolana substrate, is treated at the 10 cm-high stage by spraying with the above aqueous suspension.

Seedlings, used as controls, are treated with an aqueous solution which does not contain the active material.

After 24 hours, an aqueous suspension of spores (100,000 sp/cm$^3$) is sprayed on the wheat; this suspension was obtained from infected seedlings. The wheat is then placed for 24 hours in an incubation cell at approximately 20° C. and at 100% relative humidity, and then for 7 to 14 days at 60% relative humidity.

Monitoring of the condition of the seedlings is carried out between the 8th and 15th day after infection, by comparison with an untreated control.

Under these conditions, at a dose of 1 g/l, a good (at least 75%) or total protection is observed with the following compounds: 22, 35, 37, 31, 32, 204, 206, 207, 213, 218, 221, 223, 225, 238, 239, 246, 248, 251, 253, 294, 307, 316, 322.

These results clearly show the good fungicidal properties of the derivatives according to the invention against plant fungal diseases due to fungi belonging to the most diverse families, such as the Phycomycetes, Basidiomycetes, Ascomycetes, Adelomycetes or Fungi Imperfecti, in particular the Botrytis species, Pyricularia oryzae and grape downy mildew.

In fact, the compounds according to the invention are rarely used alone in practice. These compounds are most often part of compositions. These compositions, which can be used as fungicidal agents, contain a compound according to the invention, as described earlier, as active material mixed with solid or liquid vehicles, which are acceptable in agriculture, and surface-active agents which are also acceptable in agriculture. In particular, the inert and conventional vehicles and the conventional surface-active agents can be used. These compositions also form part of the invention.

These compositions can also contain any kind of other ingredients such as, for example, protective colloids, adhesives, thickening agents, thixotropic agents, penetrating agents, stabilising agents, sequestering agents and the like. More generally, the compounds used in the invention can be combined with all the solid or liquid additives corresponding to the conventional formulating techniques.

Generally, the compositions according to the invention usually contain from approximately 0.05 to 95% (by weight) of a compound according to the invention (subsequently called active material), one or more solid or liquid vehicles and, optionally, one or more surface-active agents.

In the present account, the term "vehicle" denotes a natural or synthetic, organic or inorganic material with which the compound is combined to facilitate its application on the plant, on seeds or on the ground. This vehicle is thus generally inert and it must be acceptable in agriculture, especially on the treated plant. The vehicle can be solid (clays, natural or synthetic silicates, silica, resins, waxes, solid fertilisers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, (especially alkylphenols or arylphenols), salts of esters of sulphosuccinic acids, taurine derivatives (especially alkyltaurates), phosphoric esters of polyoxyethylated phenols or alcohols, esters of fatty acids and of polyols, and the derivatives of the above compounds containing sulphate, sulphonate and phosphate functional groups. The presence of at least one surface-active agent is generally indispensable when the compound and/or the inert vehicle is/are not soluble in water and the carrier agent for application is water.

The compositions for agricultural use according to the invention can thus contain the active materials according to the invention within very wide limits, ranging from 0.05% to 95% (by weight). Their surface-active agent content is advantageously between 5% and 40% by weight.

These compositions according to the invention are themselves in fairly diverse, solid or liquid forms.

There may be mentioned, as forms of solid compositions, the powders for dusting (with a compound content which can range up to 100%) and the granules, especially those obtained by extrusion, by compacting, by impregnation of a granulated support, or by granulation from a powder (the compound content in these granules being between 0.5 and 80% for the latter cases), the tablets or effervescent tablets.

The compounds of formula (I) can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsifiable concentrates, emulsions, suspension concentrates, aerosols, wettable powders (or powder to be sprayed), pastes or gels.

The emulsifiable or soluble concentrates most often comprise 10 to 80% of active material while emulsions or solutions ready for application contain 0.001 to 20% of active material.

In addition to the solvent, the emulsifiable concentrates can contain, when this is necessary, 2 to 20% of suitable additives such as stabilising agents, surface-active agents, penetrating agents, corrosion inhibitors, dyes or the above-mentioned adhesives.

From these concentrates, it is possible to obtain, by dilution with water, emulsions of any desired concentration, which are particularly suitable for application to crops.

The compositions of some emulsifiable concentrates are given here as examples:

EC Example 1

| active material | 400 g/l |
| alkali metal dodecylbenzenesulphonate | 24 g/l |
| oxyethylated nonylphenol, containing 10 molecules of ethylene oxide | 16 g/l |
| cyclohexanone | 200 g/l |
| aromatic solvent | qs 1 liter |

EC Example 2

| active material | 250 g |
| epoxidised vegetable oil | 25 g |
| mixture of alkylaryl sulphonate and ether of polyglycol and fatty alcohols | 100 g |
| dimethylformamide | 50 g |
| xylene | 575 g |

The suspension concentrates, also applicable by spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilising agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition is given here as an example:

SC Example 1

| active material | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

Wettable powders (or powder to be sprayed) are generally prepared so that they contain 20 to 95% of active material, and they generally contain, in addition to the solid vehicle, from 0 to 30% of a wetting agent, from 3 to 20% of a dispersing agent and, when this is necessary, from 0.1 to 10% of one or more stabilising agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various compositions of wettable powders (or powders to be sprayed) are given here as examples:

WP Example 1

| active material | 50% |
|---|---|
| ethoxylated fatty alcohol (wetting agent) | 2.5% |
| ethoxylated phenylethylphenol (dispersing agent) | 5% |
| chalk (inert vehicle) | 42.5% |

WP Example 2

| active material | 10% |
|---|---|
| C13 branched-type synthetic oxo alcohol, ethoxylated with 8 to 10 ethylene oxide (wetting agent) | 0.75% |
| | 12% |
| neutral calcium lignosulphonate dispersing agent ) | 12% |
| calcium carbonate (inert filler) | qs 100% |

WP Example 3

This wettable powder contains the same ingredients as in the above example, in the proportions below:

| active material | 75% |
|---|---|
| wettinq agent | 1.50% |
| dispersing agent | 8% |
| calcium carbonate (inert filler) | qs 100% |

WP Example 4

| active material | 90% |
|---|---|
| ethoxylated fatty alcohol (wetting agent) | 4% |
| ethoxylated phenylethylphenol (dispersing agent) | 6% |

WP Example 5

| active material | 50% |
|---|---|
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are contained within the general scope of the present invention. Emulsions can be of the water-in-oil or oil-in-water type and they can have a thick consistency, like that of a "mayonnaise".

The compounds according to the invention can be formulated in the form of water-dispersible granules, which are also contained within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule is essentially composed of a solid filler and, optionally, of surface-active adjuvants which confer water-dispersibility properties on the granule. These granules can be essentially of two distinct types according to whether the filler held is soluble or insoluble in water. When the filler is water-soluble, it can be inorganic or, preferably, organic. Excellent results were obtained with urea. In the case of an insoluble filler, the latter is preferably inorganic, such as, for example, kaolin or bentonite. It is then advantageously accompanied by surface-active agents (in a proportion of 2 to 20% by weight of the granule) of which more than half consist of, for example, at least one dispersing agent, essentially anionic, such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Moreover, although this is not absolutely necessary, it is possible to add other adjuvants such as antifoaming agents.

The granule according to the invention can be prepared by mixing the necessary ingredients and then granulating according to several techniques known per se (granulator, fluid bed, sprayer, extrusion, and the like). The preparation generally finishes with a crushing followed by a sieving to the particle size chosen within the limits mentioned above.

It is preferably obtained by extrusion, by carrying out the preparation as indicated in the examples below.

DG Example 1

Dispersible granules

90% by weight of active material and 10% of urea in the form of pearls are mixed in a mixer. The mixture is then milled in a pin mill. A powder is obtained which is moistened with approximately 8% by weight of water. The moist powder is extruded in a perforated-roller extruder. A granule is obtained which is dried, and then crushed and sieved, so as to keep respectively only the granules having a size of between 150 and 2000 microns.

DG Example 2

Dispersible granules

The following constituents are mixed in a mixer:

| active material | 75% |
|---|---|
| wetting agent (sodium alkylnaphthalene-sulphonate) | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved so as to obtain granules having a size of between 0.15 and 0.80 mm.

These granules can be used alone or in solution or dispersion in water so as to obtain the required dose. They can also be used to prepare combinations with other active materials, especially fungicides, the latter being in the form of wettable powders or granules or aqueous suspensions.

As regards the compositions which are suitable for storage and transportation, they most advantageously contain from 0.5 to 95% (by weight) of active substance.

Another subject of the invention is the use of the compounds according to the invention for combating fungal diseases in plants by preventive or curative treatment, on the foliage or the propagation material, of the latter or of their growth site.

What is claimed is:

1. A compound having the formula (I):

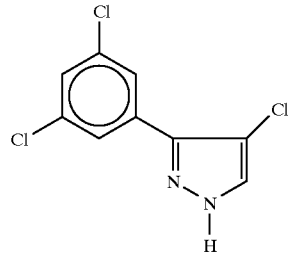
(I)

or a tautomeric form of a compound of formula (I), said tautomeric form having the formula (Ia):

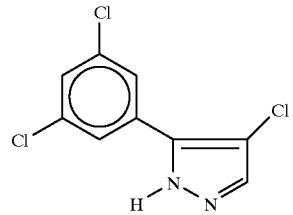
(Ia)

or a hydracid salt, a perchloric, nitric or sulphuric acid salt, an alkylsulphonic acid salt, a phenylsulphonic acid salt, or a metal or metalloid complex of a compound of formula (I) or of formula (Ia).

2. The compound as claimed in claim 1, which is 4-chloro-3-(3,5-dichlorophenyl)-1H-pyrazole.

3. The compound as claimed in claim 1, which is 4-chloro-3-(3,5-dichlorophenyl)pyrazole hemihydrochloride.

4. A fungicidal composition for protecting plants against fungal disease, said composition comprising:

(a) a fungicidally effective amount of a compound having the formula (I):

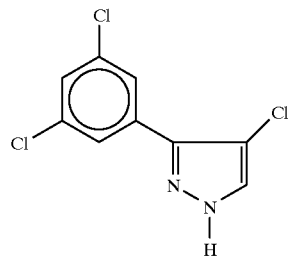
(I)

or a tautomeric form of a compound of formula (I), said tautomeric form having the formula (Ia):

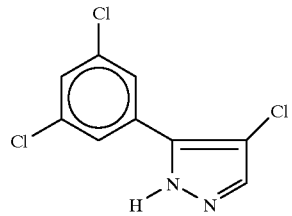
(Ia)

or a hydracid salt, a perchloric, nitric or sulphuric acid salt, an alkylsulphonic acid salt, a phenylsulphonic acid salt, or a metal or metalloid complex of a compound of formula (I) or of formula (Ia); and (b) an agriculturally acceptable vehicle.

5. A fungicidal composition as claimed in claim 4, further comprising an agriculturally acceptable surface-active agent.

6. A fungicidal composition as claimed in claim 4, where the compound is 4-chloro-3-(3,5-dichlorophenyl)-1H-pyrazole.

7. A fungicidal composition as claimed in claim 4, wherein the compound is 4-chloro-3-(3,5-dichlorophenyl) pyrazole hemihydrochloride.

8. A method for combating fungal disease in plants, said method comprising applying to said plants or to the locus in which they grow, a fungicidally effective amount of a compound having the formula (I):

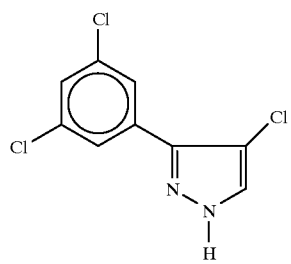
(I)

or a tautomeric form of a compound of formula (I), said tautomeric form having the formula (Ia):

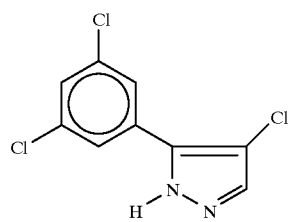
(Ia)

or a hydracid salt, a perchloric, nitric or sulphuric acid salt, an alkylsulphonic acid salt, a phenylsulphonic acid salt, or a metal or metalloid complex of a compound of formula (I) or of formula (Ia).

9. A method as claimed in claim 8, wherein the compound is 4-chloro-3-(3,5-dichlorophenyl)-1H-pyrazole.

10. A method as claimed in claim 8, wherein the compound is 4-chloro-3-(3,5-dichlorophenyl)pyrazole hemihydrochloride.

11. A process for preparing a compound as claimed in claim 1, said process comprising chlorinating a compound having the formula (III):

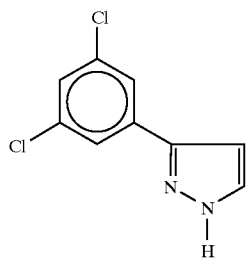

(III)

with a chlorinating agent.

12. A process as claimed in claim 11, wherein the reaction is conducted in an aqueous or organic solution.

13. A process as claimed in claim 12, wherein the chlorinating agent is chlorine, hypochlorous acid, hydrochloric acid in the presence of hydrogen peroxide, sulphuryl chloride, or phosphorus pentachloride.

14. A process as claimed in claim 12, wherein the chlorinating agent is an N-chloroimide.

15. A process according to claim 14, wherein the N-chloroimide is N-chlorosuccininide.

* * * * *